United States Patent [19]

Serban et al.

[11] Patent Number: 5,110,989
[45] Date of Patent: May 5, 1992

[54] HERBICIDAL COMPOUNDS AND COMPOSITIONS

[75] Inventors: Alexander Serban, Doncaster; Keith G. Watson, Box Hill North; Graham J. Bird, North Melbourne; Graeme J. Farquharson, Reservoir; Linsay E. Cross, Maribyrnong, all of Australia

[73] Assignee: ICI Australia Limited, Melbourne, Australia

[21] Appl. No.: 553,413

[22] Filed: Jul. 17, 1990

Related U.S. Application Data

[62] Division of Ser. No. 461,003, Jan. 26, 1983, Pat. No. 4,952,722.

[30] Foreign Application Priority Data

Feb. 12, 1982 [AU] Australia .............................. PF2693
Jul. 2, 1982 [AU] Australia .............................. PF4686

[51] Int. Cl.$^5$ .......................................... C07C 49/115
[52] U.S. Cl. .................................. 568/327; 558/54; 558/57; 558/60; 558/62; 558/414; 558/419; 560/53; 560/139; 564/102; 564/169; 564/194; 564/195; 564/265
[58] Field of Search .................... 568/327; 558/54, 57, 558/60, 62, 414, 419; 560/53, 139; 564/102, 109, 194, 195; 564/268

[56] References Cited

PUBLICATIONS

1980 British Crop Protection Conference—Weeds, Proceedings vol. 1, Research Report.

*Primary Examiner*—Paul J. Killos
*Attorney, Agent, or Firm*—Cushman, Darby & Cushman

[57] ABSTRACT

The invention concerns novel compounds of the formula I

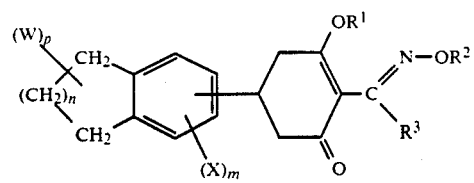

wherein:
W are selected from alkyl, alkenyl and alkynyl;
X are selected from halogen, nitro, cyano, alkyl, substituted alkyl, hydroxy, alkoxy, substituted alkoxy, alkenyl, alkynyl, alkenyloxy, alkynyloxy, acyloxy, alkoxycarbonyl, alkylthio, alkylsulfinyl, alkylsulfonyl, sulfamoyl, substituted sulfamoyl, amino, substituted amino, and the groups formyl and alkanoyl and the oxime, imine and Schiff base derivatives thereof, and an alkylene group which bridges two adjacent carbon atoms of the benzene ring;
$R^1$ is selected from hydrogen, alkyl, alkenyl, alkynyl, substituted alkyl, alkylsulfonyl, arylsulfonyl, acyl and an inorganic or organic cation;
$R^2$ is selected from alkyl, substituted alkyl, alkenyl, haloalkenyl, alkynyl and haloalkynyl;
$R^3$ is selected from alkyl, fluoroalkyl, alkenyl, alkynyl, and phenyl;
p is zero or an integer selected from 1 to 4;
n is zero or an integer selected from 1 to 3; and
m is zero or an integer selected from 1 to 3.

The compounds of the invention show cereal selective herbicidal properties and plant growth regulating properties and in further embodiments the invention provides processes for the preparation of the compounds of formula I, intermediates useful in the preparation of the compounds of formula I, compositions containing as active ingredient a compound of formula I, and herbicidal and plant growth regulating processes utilizing compounds of formula I.

2 Claims, No Drawings

HERBICIDAL COMPOUNDS AND COMPOSITIONS

This is a division of application Ser. No. 06/461,003, filed Jan. 26, 1983 now U.S. Pat. No. 4,952,722.

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes using such compounds.

The use of certain cyclohexane-1,3-dione derivatives as grass herbicides is known in the art. For example, the "Pesticide Manual" (C R Worthing Editor, The British Crop Protection Council, 6th Edition 1979) describes the cyclohexane-1,3-dione derivative known commercially as alloxydim-sodium (methyl 3-[1-allyloxyimino)-butyl]-4-hydroxy-6,6-dimethyl-2-oxocyclohex-3-ene-carboxylate) and its use as a grass herbicide. This compound is disclosed in Australian Patent No 464 655 and its equivalents such as UK Patent No 1 461 170 and U.S. Pat. No. 3,950,420.

More recently, at the 1980 British Crop Protection Conference ("1980 British Crop Protection Conference—Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No AU-Al-35,314/78 and its equivalents.

As indicated above, both alloxydim-sodium and NP 55 are grass herbicides, that is, herbicides which selectively control the growth of grass weeds (monocotyledonous plants) in broad-leaved crops (dicotyledonous plants).

At the 1978 International Union of Pure and Applied Chemistry Fourth International Congress of Pesticide Chemistry ("Advances in Pesticide Science—Part 2", pp 235–243, Pergamon Press, 1979), in a paper discussing the chemical structure and herbicidal activity of alloxydim-sodium, Iwataki and Hirono made the following disclosure about the herbicidal selectivity between wheat and oats of certain 5-phenyl substituted cyclohexane-1,3-dione derivatives: "When substituted phenyl groups were introduced at the C-5 position (Table 6), the selectivity between wheats and oats such as Avena fatua and Avena sativa was observed. The selectivity was found only in the case of para-substituents at the phenyl nucleus and the effect was not found in the case of di- or tri- substitution. Even in the para-substituents, the degree of activity or selectivity was different. The best result was obtained when the methyl group was introduced at the para-position and the hydroxy or the methoxy derivative gave moderately good results."

It has now been found that certain novel 5-aryl substituted cyclohexan-1,3-dione derivatives exhibit particularly useful cereal selective herbicidal activity and plant growth regulating activity.

Accordingly the invention provides a compound of formula I:

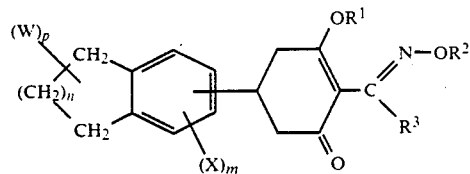

wherein:

W, which may be the same or different, are selected from the group consisting of $C_1$ to $C_6$ alkyl, $C_2$ to $C_6$ alkenyl and $C_2$ to $C_6$ alkynyl;

X, which may be the same or different, are selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy) carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^8R^9$ wherein $R^8$ and $R^9$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof; and the group $-(CH_2)_q-$ which bridges two adjacent carbon atoms of the benzene ring and wherein q is an integer selected from 2 to 5;

$R^1$ is chosen from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent chosen from the group consisting of $C_1$ to $C_6$ alkoxy, $C_1$ to $C_6$ alkylthio, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzenesulfonyl; substituted benzenesulfonyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is chosen from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent chosen from the group consisting of halogen, $C_1$ to $C_6$ alkoxy, $C_1$ to $C_6$ alkylthio, phenyl and substituted phenyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is chosen from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

p is zero or an integer chosen from 1 to 4;

n is zero or an integer chosen from 1 to 3; and m is zero or an integer chosen from 1 to 3.

When in the compound of formula I X is chosen from the group formyl and $C_2$ to $C_6$ alkanoyl and the oxime, and imine (Schiff base) derivatives thereof, the nature of the oxime and imine derivatives is not narrowly critical. Although not intending to be bound by theory, it is believed that in the plant the (substituted) imine group may be removed to give the corresponding compound of formula I in which X is formyl or $C_2$ to $C_6$ alkanoyl. Suitable values for the groups formyl and $C_2$ to $C_6$ alkanoyl and the oxime, imine and Schiff base derivatives thereof include groups of the formula $—C(R^{10})=NR^{11}$ wherein $R^{10}$ is chosen from hydrogen and $C_1$ to $C_5$ alkyl and $R^{11}$ is chosen from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cations is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^4R^5R^6R^7N^\oplus$ wherein $R^4$, $R^5$, $R^6$ and $R^7$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^1$ is hydrogen the compounds of the invention may exist in any one of three tautomeric forms as shown below.

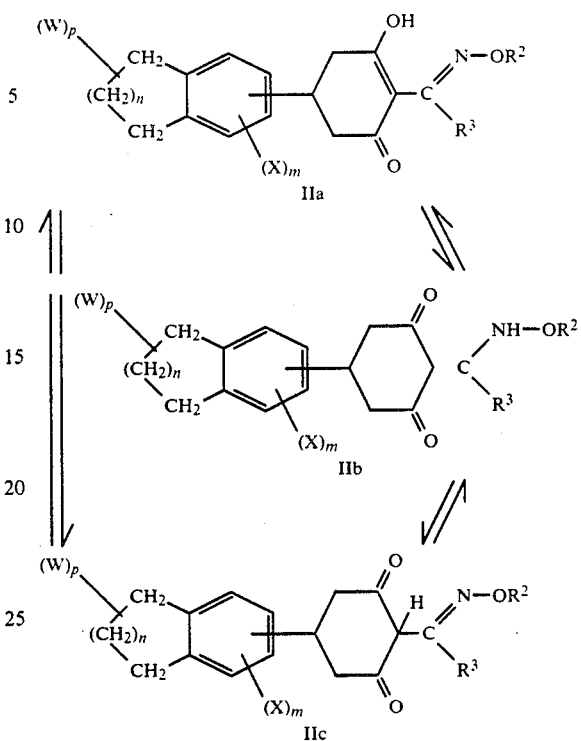

Suitable X include halogen, nitro, cyano, $C_1$ to $C_6$ alkyl and $C_1$ to $C_6$ alkoxy.

Suitable $R^1$ include hydrogen, benzoyl, substituted benzoyl wherein the benzene ring is substituted with from one to three substituents chosen from the group consisting of halogen, nitro, $C_1$ to $C_6$ alkyl, $C_1$ to $C_6$ alkoxy and $C_1$ to $C_6$ haloalkyl, and the group M wherein M is an alkali metal ion.

Suitable $R^2$ include $C_1$ to $C_6$ alkyl, $C_2$ to $C_6$ alkenyl, $C_2$ to $C_6$ alkynyl, benzyl and substituted benzyl wherein the benzene ring is substituted with from one to three substituents chosen from the group consisting of halogen, nitro, $C_1$ to $C_6$ alkyl, $C_1$ to $C_6$ alkoxy and $C_1$ to $C_6$ haloalkoxy.

Suitable $R^3$ include $C_1$ to $C_6$ alkyl.

Suitable n include zero or an integer chosen from 1 to 3.

Suitable m include zero or an integer chosen from 1 and 2.

Preferred W include $C_1$ to $C_3$ alkyl.

Preferred X include: halogen; nitro; cyano; hydroxy; $C_1$ to $C_4$ alkyl; $C_1$ to $C_4$ alkoxy; $C_2$ to $C_4$ alkenyloxy; $C_1$ to $C_4$ alkylthio; $C_1$ to $C_4$ alkylsulfinyl; $C_1$ to $C_4$ alkylsulfonyl; formyl, $C_2$ to $C_6$ alkanoyl and the oxime O-$C_1$ to $C_4$ alkyl ethers thereof; $C_2$ to $C_6$ alkanoyloxy; benzyloxy; sulfamoyl; N,N-di($C_1$ to $C_4$ alkyl)sulfamoyl; $C_1$ to $C_4$ alkyl substituted with a substituent selected from the group consisting of nitro, hydroxy, $C_1$ to $C_4$ alkoxy and $C_1$ to $C_4$ alkylthio; $C_1$ to $C_4$ alkoxy substituted with one or more substituents selected from halogen; the group $NR^8R^9$ wherein $R^8$ and $R^9$ are independently selected from hydrogen and $C_2$ to $C_4$ alkanoyl; and the group $—(CH_2)_q—$ which bridges two adjacent carbon atoms of the benzene ring and wherein q is an integer selected from 3 and 4.

Preferred $R^1$ include: hydrogen; $C_2$ to $C_6$ alkanoyl such as acetyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substitutents selected from the group consisting of halogen, nitro, $C_1$ to $C_6$ alkyl and $C_1$ to $C_6$ alkoxy; and an inorganic or organic cation selected from the cations of the alkali metals such as lithium, potassium and sodium, the cations of the alkaline earth metals such as magnesium, calcium and barium, the cations of the transition metals such as manganese, copper, zinc, iron, nickel, cobalt and silver, the ammonium ion and the triand tetra-(alkyl) ammonium ions wherein alkyl is selected from $C_1$ to $C_6$ alkyl and $C_1$ to $C_6$ hydroxyalkyl.

Preferred $R^2$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; and $C_2$ to $C_6$ haloalkynyl.

Preferred $R^3$ include $C_1$ to $C_6$ alkyl.

Preferred n is an integer chosen from 1 and 2.

More preferred compounds of the invention include those compounds of formula I in which n is 1. That is compounds of formula

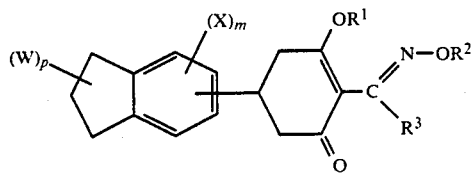

wherein:
W is methyl;
X is selected from the group consisting of halogen, $C_1$ to $C_4$ alkyl, $C_1$ to $C_4$ alkoxy, $C_1$ to $C_4$ alkylthio, sulfamoyl, N,N-di($C_1$ to $C_4$ alkyl)sulfamoyl, and the group —(CH$_2$)$_3$— which bridges two adjacent carbon atoms of the benzene ring;
$R^1$ is selected from the group consisting of hydrogen, acetyl, benzoyl, substituted benzoyl wherein the benzene ring is substituted with a substituent chosen from nitro, halogen, methyl and methoxy, benzenesulfonyl, substituted benzenesulfonyl wherein the benzene ring is substituted with a substituent chosen from nitro, halogen, methyl and methoxy, the cations of the alkali metals, the cations of the transition metals, the ammonium ion and the tri- and tetra-(alkyl) ammonium ions wherein alkyl is selected from $C_1$ to $C_6$ alkyl and $C_1$ to $C_6$ hydroxyalkyl;
$R^2$ is selected from the group consisting of $C_1$ to $C_3$ alkyl, $C_1$ to $C_3$ haloalkyl, allyl and haloallyl;
$R^3$ is selected from $C_1$ to $C_3$ alkyl;
p is zero or an integer chosen from 1 to 3; and
m is zero or an integer chosen from 1 to 3.

Included among the more preferred compounds of the invention are those 4-indanyl compounds which are further substituted in the 7-position of the indane ring. That is, compounds of formula

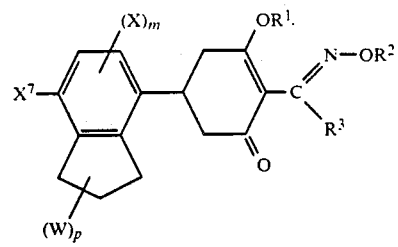

wherein:
W is methyl;
X and $X^7$ are independently selected from the group consisting of methyl, methoxy and halogen;
$R^1$ is selected from the group consisting of hydrogen, acetyl, benzoyl, nitrobenzoyl, methylbenzenesulfonyl and the cations of the alkali metals;
$R^2$ is selected from the group consisting of $C_1$ to $C_3$ alkyl, 2-haloethyl, allyl and 2-haloallyl;
$R^3$ is selected from $C_1$ to $C_3$ alkyl;
p is zero or an integer chosen from 1 and 2; and
m is zero or an integer chosen from 1 and 2.

Also included among the more preferred compounds of the invention are those 5-indanyl compounds which are further substituted in at least one of the 4- and 6- positions of the indane ring. That is, compounds of formula

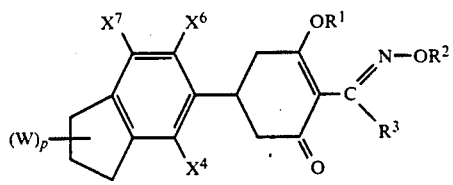

wherein:
W is methyl;
$X^4$ and $X^6$ are independently selected from the group consisting of hydrogen, methyl, methoxy and halogen and at least one of $X^4$ and $X^6$ is not hydrogen;
$X^7$ is selected from the group consisting of hydrogen, methyl, methoxy, halogen and N,N-di(methyl)sulfamoyl;
$R^1$ is selected from the group consisting of hydrogen, acetyl, benzoyl, nitrobenzoyl, methylbenzenesulfonyl and the cations of the alkali metals;
$R^2$ is selected from the group consisting of $C_1$ to $C_3$ alkyl, 2-haloethyl, allyl and 2-haloallyl;
$R^3$ is selected from $C_1$ to $C_3$ alkyl; and
p is zero or an integer chosen from 1 and 2.

Included among the even more preferred compounds of the invention are those 4-indanyl compounds which are further substituted in the 5- and 7-positions of the indane ring. That is, compounds of formula

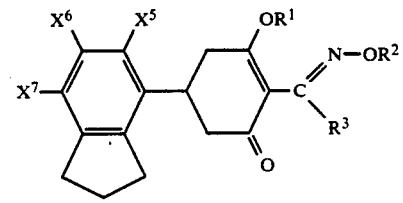

wherein:

$X^5$ is selected from the group consisting of methyl, methoxy and halogen;
$X^6$ is selected from the group consisting of hydrogen, methyl, methoxy and halogen;
$X^7$ is methyl;
$R^1$ is selected from the group consisting of hydrogen, acetyl, sodium and potassium;
$R^2$ is selected from ethyl and allyl; and
$R^3$ is selected from ethyl and n-propyl.

Also included among the even more preferred compounds of the invention are those 5-indanyl compounds which are further substituted in the 4- and 6-positions of the indane ring. That is compounds of formula

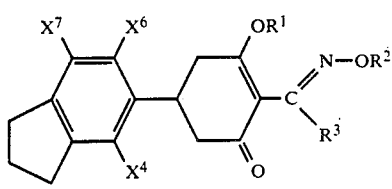

wherein:
$X^4$ and $X^6$ are independently selected from the group consisting of methyl, methoxy and halogen;
$X^7$ is selected from the group consisting of hydrogen, methyl, methoxy and halogen;
$R^1$ is selected from the group consisting of hydrogen, acetyl, sodium and potassium;
$R^2$ is selected from ethyl and allyl; and
$R^3$ is selected from ethyl and n-propyl.

Specific examples of the compounds of the invention include those compounds detailed in Tables 1a to 1e.

TABLE 1a

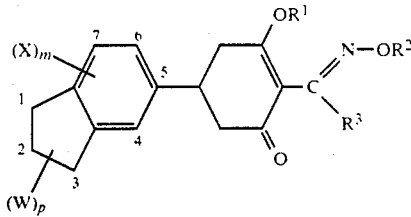

| Compound No | $(X)_m + (W)_p$ | $R^1$ | $R^2$ | $R^3$ |
|---|---|---|---|---|
| 1 | H | H | $C_2H_5$ | $C_2H_5$ |
| 2 | H | Na+ | $C_2H_5$ | $C_2H_5$ |
| 3 | H | a | $C_2H_5$ | $C_2H_5$ |
| 4 | H | H | $CH_2CH=CH_2$ | $C_2H_5$ |
| 5 | H | H | $C_2H_5$ | n-$C_3H_7$ |
| 6 | H | H | $CH_2CH=CH_2$ | n-$C_3H_7$ |
| 8 | 4,7-$(CH_3)_2$ | H | $C_2H_5$ | $C_2H_5$ |
| 9 | 4,6-$(CH_3)_2$ | H | $C_2H_5$ | $C_2H_5$ |
| 11 | 4,6,7-$(CH_3)_3$ | H | $C_2H_5$ | $C_2H_5$ |
| 13 | 7-Br-4,6-$(CH_3)_2$ | H | $C_2H_5$ | $C_2H_5$ |
| 14 | 2,2,4,7-$(CH_3)_4$ | H | $C_2H_5$ | $C_2H_5$ |
| 15 | 2,2,4,6,7-$(CH_3)_5$ | H | $C_2H_5$ | $C_2H_5$ |
| 16 | 2,2-$(CH_3)_2$ | H | $C_2H_5$ | $C_2H_5$ |
| 17 | 4,6-$(CH_3)_2$-7-$SO_2N(CH_3)_2$ | H | $C_2H_5$ | $C_2H_5$ |
| 18 | 4,7-$(CH_3)_2$-6-$SO_2N(CH_3)_2$ | H | $C_2H_5$ | $C_2H_5$ |
| 19 | 6-Br-4,7-$(CH_3)_2$ | H | $C_2H_5$ | $C_2H_5$ |
| 20 | 4,7-$(CH_3)_2$-6-$C_2H_5$ | H | $C_2H_5$ | $C_2H_5$ |
| 21 | 7-Cl-4,6-$(CH_3)_2$ | H | $C_2H_5$ | $C_2H_5$ |
| 22 | 4-Cl-6,7-$(CH_3)_2$ | H | $C_2H_5$ | $C_2H_5$ |
| 23 | 6-Br-4,7-$(CH_3)_2$ | H | $C_2H_5$ | n-$C_3H_7$ |
| 24 | 6-Cl-4,7-$(CH_3)_2$ | H | $C_2H_5$ | n-$C_3H_7$ |
| 25 | 6-Cl-4,7-$(CH_3)_2$ | H | $C_2H_5$ | $C_6H_5$ |
| 46 | 2-$CH_3$ | H | $C_2H_5$ | $C_2H_5$ |
| 47 | 1,1,4,6,7-$(CH_3)_5$ | H | $C_2H_5$ | $C_2H_5$ |
| 48 | 1,1,2,4,6,7-$(CH_3)_6$ | H | $C_2H_5$ | $C_2H_5$ |

TABLE 1a-continued

| Compound No | $(X)_m + (W)_p$ | $R^1$ | $R^2$ | $R^3$ |
|---|---|---|---|---|
| 49 | 1,1,2,4,6,7-$(CH_3)_6$ | H | $C_2H_5$ | n-$C_3H_7$ |
| 50 | 3,4,6,7-$(CH_3)_4$ | H | $C_2H_5$ | n-$C_3H_7$ |
| 51 | 2,4,6,7-$(CH_3)_4$ | H | $C_2H_5$ | n-$C_3H_7$ |

Footnote to Table 1a
a $C_6H_5CO$

TABLE 1b

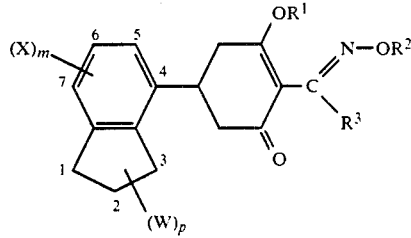

| Compound No | $(X)_m + (W)_p$ | $R^1$ | $R^2$ | $R^3$ |
|---|---|---|---|---|
| 10 | 5,7-$(CH_3)_2$ | H | $C_2H_5$ | $C_2H_5$ |
| 12 | 5,6,7-$(CH_3)_3$ | H | $C_2H_5$ | $C_2H_5$ |
| 26 | 6-Cl-5,7-$(CH_3)_2$ | H | $C_2H_5$ | $C_2H_5$ |
| 31 | 5,6,7-$(CH_3)_3$ | Na+ | $C_2H_5$ | n-$C_3H_7$ |
| 32 | 5,6,7-$(CH_3)_3$ | a | $C_2H_5$ | n-$C_3H_7$ |
| 33 | 5-Br-6,7-$(CH_3)_2$ | Na+ | $C_2H_5$ | n-$C_3H_7$ |
| 34 | 6-F-5,7-$(CH_3)_2$ | H | $C_2H_5$ | n-$C_3H_7$ |
| 35 | 6-F-5,7-$(CH_3)_2$ | Na+ | $C_2H_5$ | n-$C_3H_7$ |
| 36 | 5,6,7-$(CH_3)_3$ | Li+ | $C_2H_5$ | n-$C_3H_7$ |
| 37 | 5,6,7-$(CH_3)_3$ | $CH_3CO$ | $C_2H_5$ | n-$C_3H_7$ |
| 38 | 5,6,7-$(CH_3)_3$ | b | $C_2H_5$ | n-$C_3H_7$ |
| 39 | 5,6,7-$(CH_3)_3$ | H | c | n-$C_3H_7$ |
| 40 | 5,6,7-$(CH_3)_3$ | ½$Cu^{2+}$ | $C_2H_5$ | n-$C_3H_7$ |
| 41 | 5,6,7-$(CH_3)_3$ | ½$Ni^{2+}$ | $C_2H_5$ | n-$C_3H_7$ |
| 42 | 5,6,7-$(CH_3)_3$ | d | $C_2H_5$ | n-$C_3H_7$ |
| 43 | 5,6,7-$(CH_3)_3$ | e | $C_2H_5$ | n-$C_3H_7$ |
| 44 | 5,6,7-$(CH_3)_3$ | H | $CH_2CH_2F$ | n-$C_3H_7$ |
| 45 | 5,6,7-$(CH_3)_3$ | H | $C_2H_5$ | $C_6H_5$ |
| 52 | 2,2,5,6,7-$(CH_3)_5$ | H | $C_2H_5$ | $C_2H_5$ |
| 53 | 2,2,5,6,7-$(CH_3)_5$ | H | $C_2H_5$ | n-$C_3H_7$ |
| 54 | 3,3,5,6,7-$(CH_3)_5$ | H | $C_2H_5$ | $C_2H_5$ |
| 55 | 2,5,6,7-$(CH_3)_4$ | H | $C_2H_5$ | n-$C_3H_7$ |
| 56 | 1,5,6,7-$(CH_3)_4$ | H | $C_2H_5$ | n-$C_3H_7$ |
| 57 | 5-$CH_2CH_2CH_2$-6 | H | $C_2H_5$ | $C_2H_5$ |
| 58 | 5-$CH_2CH_2CH_2$-6 | H | $C_2H_5$ | n-$C_3H_7$ |
| 59 | 7-$CH_3$-5-$CH_2CH_2CH_2$-6 | H | $C_2H_5$ | n-$C_3H_7$ |
| 60 | 5-Br-6,7-$(CH_3)_2$ | H | $C_2H_5$ | n-$C_3H_7$ |
| 61 | 5,6,7-$(CH_3)_3$ | H | $C_2H_5$ | n-$C_3H_7$ |

Footnotes to Table 1b
a $C_6H_5CO$
b 4-$CH_3C_6H_4SO_2$
c $CH_2CBr=CH_2$
d 4-$NO_2C_6H_4CO$
e $N(n-C_4H_9)_4$

TABLE 1c

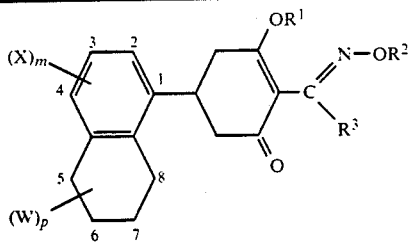

| Compound No | $(X)_m + (W)_p$ | $R^1$ | $R^2$ | $R^3$ |
|---|---|---|---|---|
| 27 | 2,3,4-$(CH_3)_3$ | H | $C_2H_5$ | $C_2H_5$ |
| 28 | 2,3,4-$(CH_3)_3$ | H | $C_2H_5$ | n-$C_3H_7$ |
| 30 | 3,4-$(CH_3)_2$-2-$OCH_3$ | H | $C_2H_5$ | n-$C_3H_7$ |

TABLE 1d

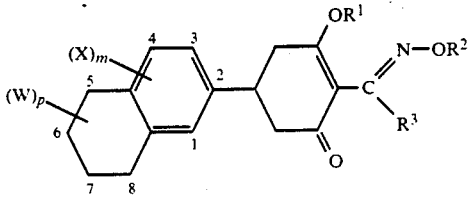

| Compound No | $(X)_m + (W)_p$ | $R^1$ | $R^2$ | $R^3$ |
|---|---|---|---|---|
| 7 | H | H | $C_2H_5$ | $C_2H_5$ |

TABLE 1e

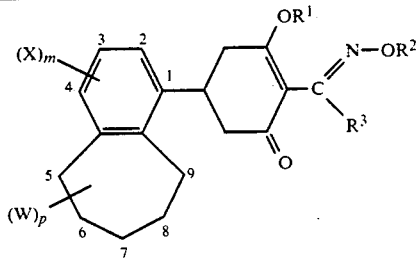

| Compound No | $(X)_m + (W)_p$ | $R^1$ | $R^2$ | $R^3$ |
|---|---|---|---|---|
| 29 | 2,3,4-$(CH_3)_3$ | H | $C_2H_5$ | n-$C_3H_7$ |

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 5-(substituted aryl)cyclohexane-1,3-dione of formula IX. This reaction may be carried out in a two step process by condensing an aldehyde derivative of formula V with acetone to form a ketone of formula VI, which is in turn condensed with a malonic acid ester of formula VII to give a 5-(substituted aryl)cyclohexane-1,3-dione of formula IX, either with or without the isolation of the intermediate of formula VIII.

Alternatively, this preparation may be carried out in a two step process by condensing an aldehyde derivative of formula V with a malonic acid ester of formula VII to give an arylmethylidenemalonate derivative of formula X which is in turn condensed with an acetoacetic acid ester of formula XI to give a 5-(substituted aryl)cyclohexane-1,3-dione of formula IX, either with or without isolation of the intermediate of formula XII.

In a further alternative process this preparation may be carried out by condensing a 2-arylalkenoate derivative of formula XXI with an acetoacetic acid ester of formula XI to give a 5-(substituted aryl)cyclohexan-1,3-dione of formula IX, either with or without isolation of the intermediate of formula VIII.

The above reaction sequences are set out in SCHEME A parts (i), (ii) and (iii) respectively below, wherein R represents a $C_1$ to $C_6$ alkyl group.

SCHEME A

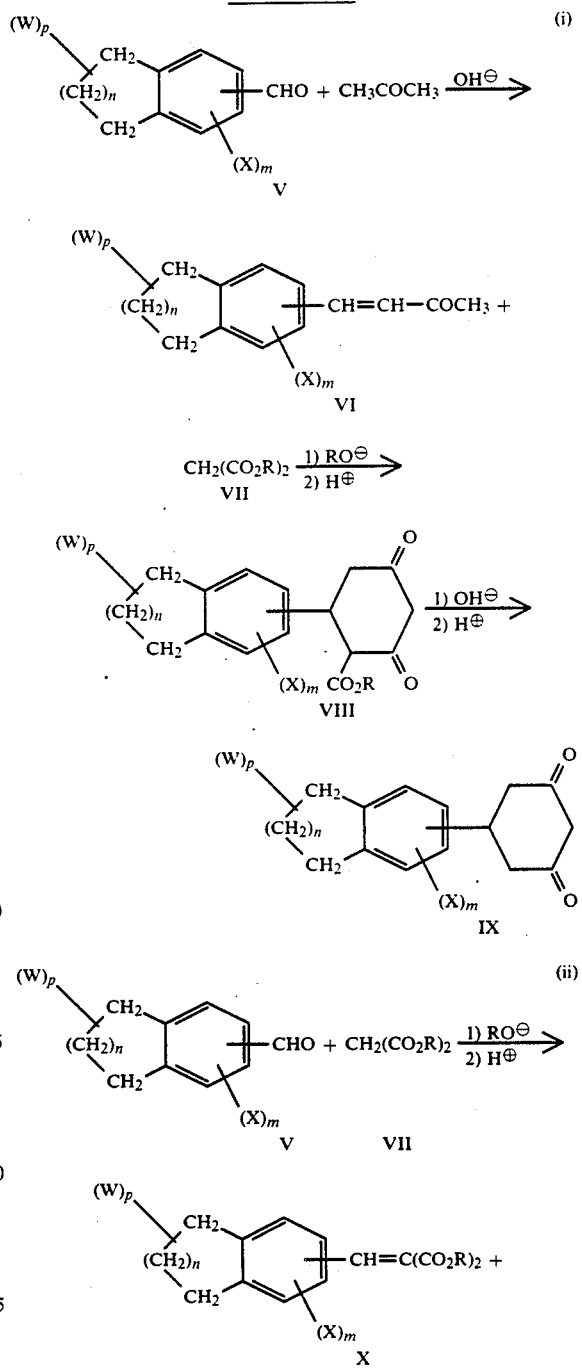

-continued
SCHEME A

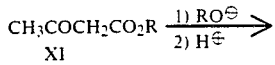

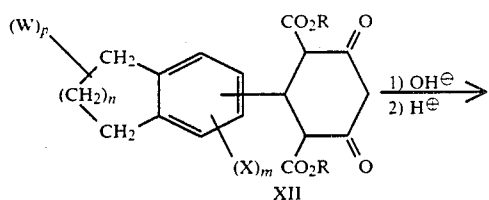

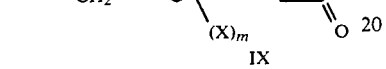

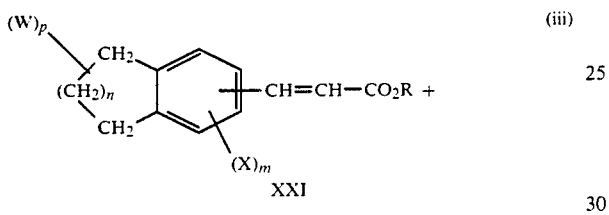

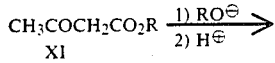

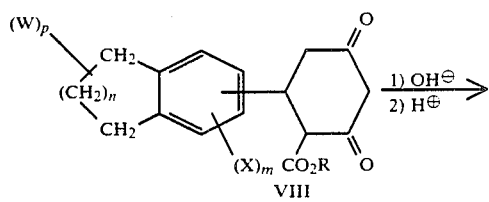

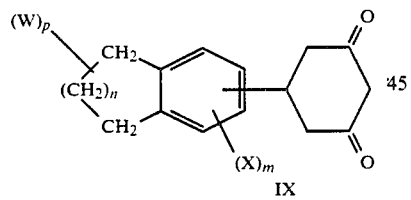

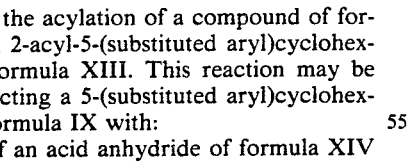

Part B involves the acylation of a compound of formula IX to give a 2-acyl-5-(substituted aryl)cyclohexane-1,3-dione of formula XIII. This reaction may be carried out by reacting a 5-(substituted aryl)cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV;

(vii) a mixture of an acid halide of formula XV and the corresponding acid; or (viii) an alkali metal or alkaline earth metal hydride followed by reaction with an acid anhydride of formula XIV or an acid chloride of formula XV.

Alternatively this reaction may be carried out by:

(ix) reacting a 5-(substituted aryl)cyclohexane-1,3-dione of formula IX with an acid halide of formula XV in the presence of pyridine to give an intermediate O-acyl derivative of formula XVI; and (x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

SCHEME B

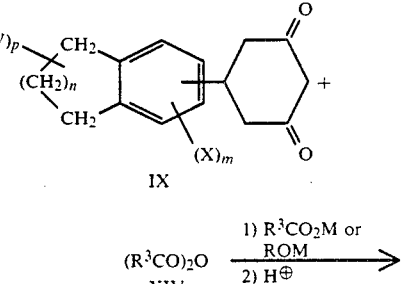

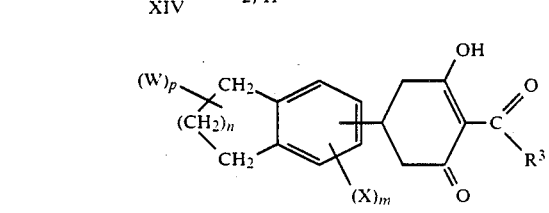

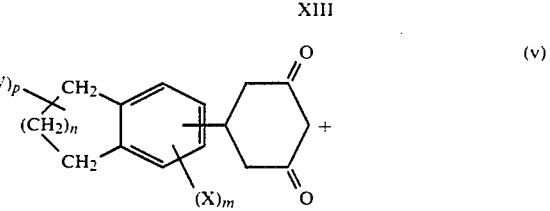

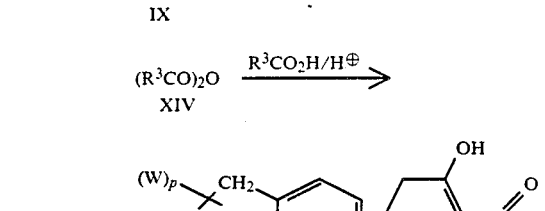

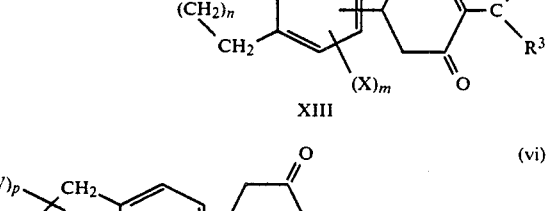

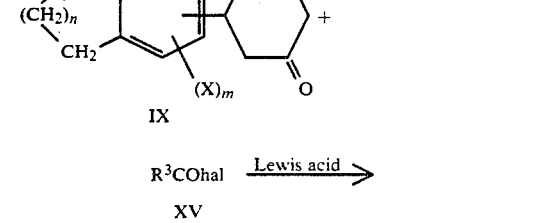

-continued
SCHEME B
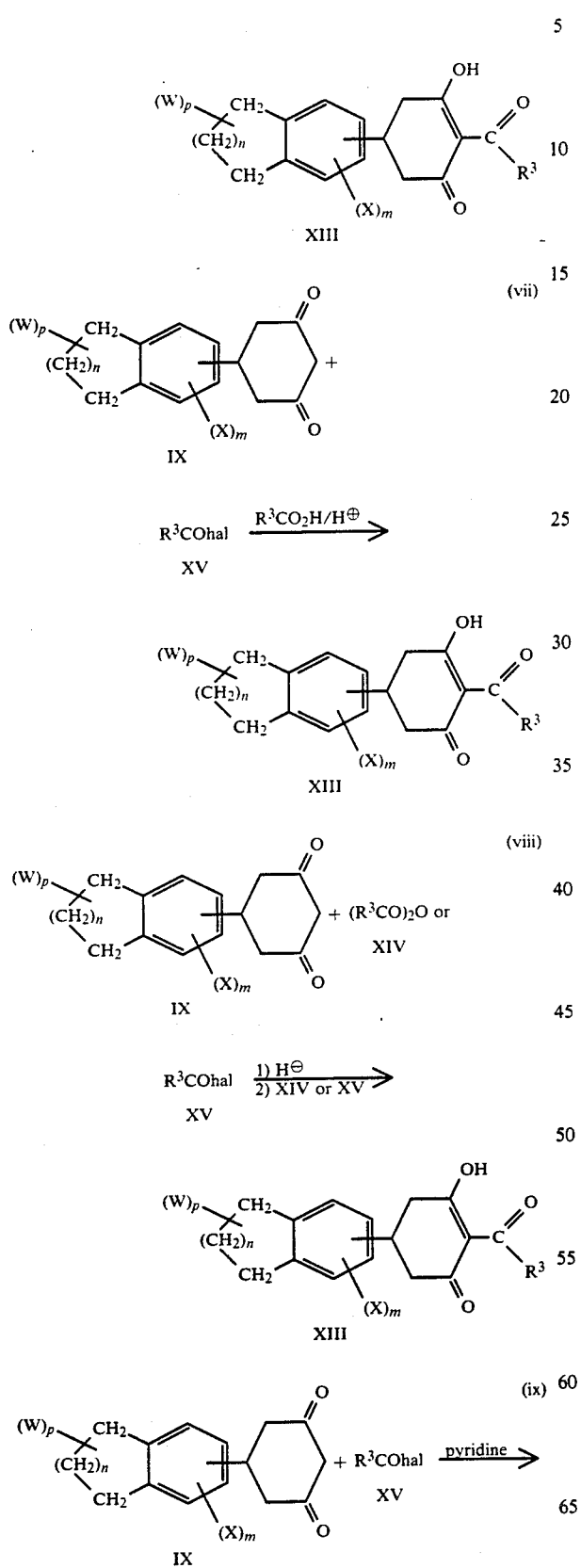
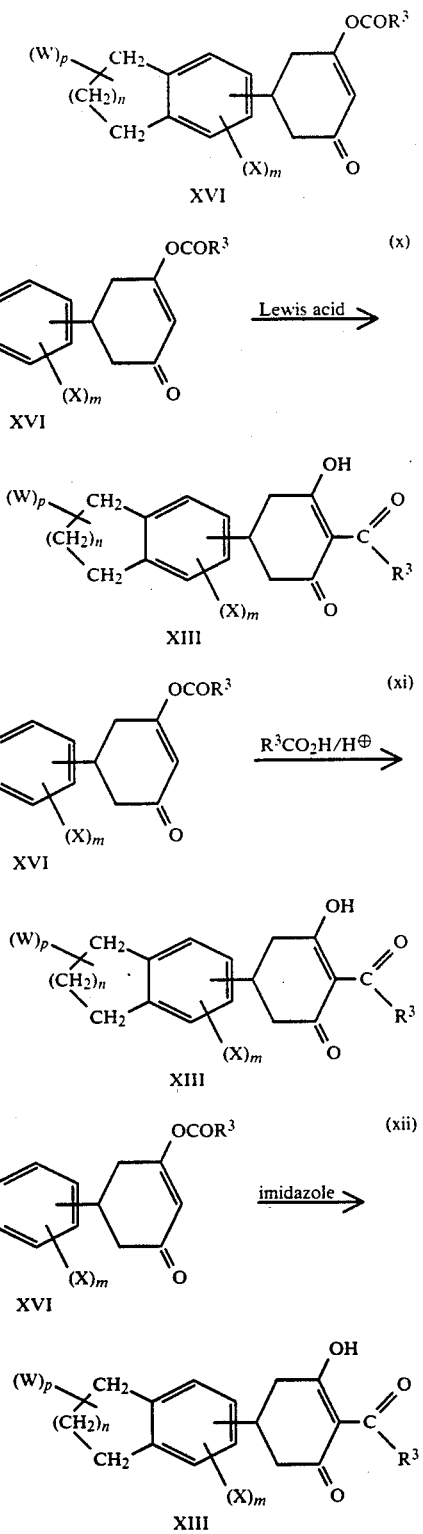
Part C involves the formation of a compound of the invention of formula I wherein $R^1$ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

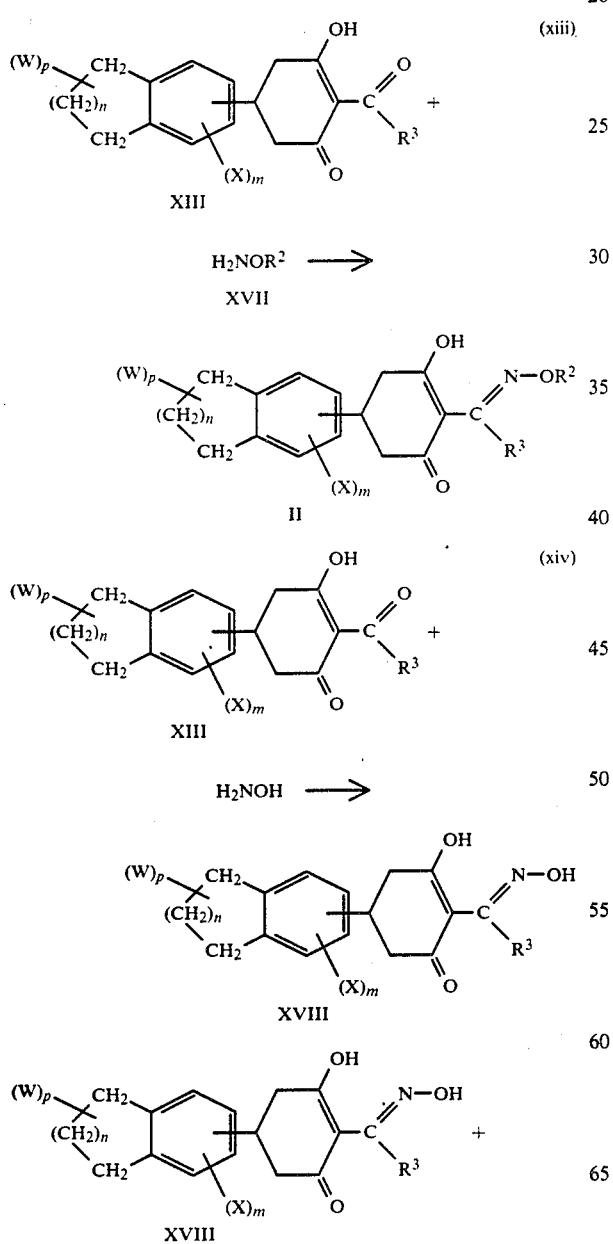

-continued
SCHEME C

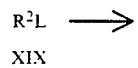

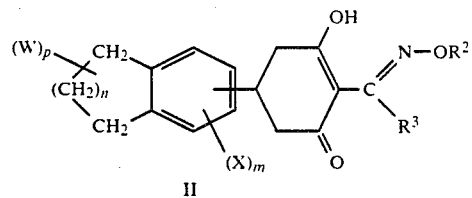

Compounds of the invention of formula I wherein $R^1$ is not hydrogen may be prepared from compounds of the invention of formula I wherein $R^1$ is hydrogen, that is, compounds of formula II, by etherification, acylation or sulfonylation as required. This reaction is outlined in SCHEME D below.

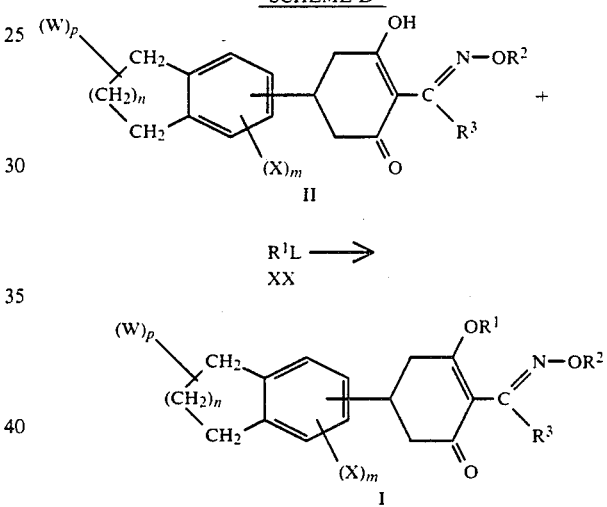

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metalion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, wherein W, X, $R^1$, $R^2$, $R^3$, p, m and n are as hereinbefore defined, which process comprises:

a) reacting an aldehyde derivative of formula V with acetone to give a ketone derivative of formula VI and reacting the ketone derivative of formula VI with a malonic acid ester of formula VII, wherein R is $C_1$ to $C_6$ alkyl, to give a 5-(substituted aryl)cyclohexane-1,3-dione derivative of formula IX; or reacting an aldehyde derivative of formula V with a malonic acid ester of formula VII to give an arylmethylidenemalonate derivative of formula X and reacting the arylmethylidenemalonate derivative of formula X with an acetoacetic acid ester fo formula XI, wherein R is $C_1$ to $C_6$ alkyl, to give a 5-(substituted aryl)cyclohexane-1,3-dione derivative of formula IX; or reacting a 2-arylalkenoate derivative of formula XXI, wherein R is $C_1$ to $C_6$ alkyl, with an acetoacetic acid ester of formula XI, wherein R is $C_1$ to $C_6$ alkyl, to give a 5-(substituted phenyl)cyclohexane-1,3-dione derivative of formula IX;

b) acylating the 5-(substituted aryl)cyclohexane-1,3-dione derivative of formula IX with an acid anhydride of formula XIV or an acid halide of formula XV to give a 2-acyl-5-(substituted aryl)cyclohexane-1,3-dione derivative of formula XIII;

c) reacting the 2-acyl-5-(substituted aryl)-cyclohexane-1,3-dione derivative of formula XIII with an alkoxyamine derivative of formula XVII to give a compound of the invention of formula II or reacting the 2-acyl-5-(substituted aryl) cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and optionally d) reacting the compound of the invention of formula II with a compound of formula XX, wherein L is a good leaving group, to give a compound of the invention of formula I.

Certain of the intermediate compounds of formula VI, VIII, IX, X, XII, XXI, XIII, XVI and XVIII are novel compounds are therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

The compounds of formula I are active as herbicides against monocotyledonous weeds, wild grasses, and in particular are selectively active against difficulty controllable wild grasses in crops of cultivated plants. The compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyldonous weeds in cultivated crops, especially wild grasses in cereal crops such as wheat and barley, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth, stimulation of early flowering and seed formation, enhancement of flowering and increase in seed yield, stem thickening, stem shortening and tillering. Plant growth regulating effects shown by compounds of the invention include, for example tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (post-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphththalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and napththalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly-(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which posses biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3-thiadiazin-4-one-2,2-dioxides such as 3-isopropylbenzo-2,1,3-thiadizin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;
E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diruon) and N,N-dimethyl-N'-[3-(trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);
H. 2-phenylpyridazin-3-ones such as 5-amino-4-chloro-2-phenylpyridazin-3-one (common name pyrazon);
I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);
J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(isopropylamino)-6-methylthio-1,3,5-triazine (common name aziproptryne);
K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);
L. thiolcarbamate herbicides such as S-propyl dipropylthiocarbamate (common name verolate);
M. 1,2,4-triazin-5-one herbicides such as 4-amino-4,5-dihydro-3-methyl-6-phenyl-1,2,4,-triazine-5-one (common name metamitron) and 4-amino-6-tert-butyl 4,5-dihydro-3-methylthio-1,3,4-triazin-5-one (common name metribuzin);
N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).
O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);
P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).
Q. haloalkanoic herbicides such as 2,2-dichloropropionic acid (common name dalapon), trichloroacetic acid (common name TCA) and salts thereof;
R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;
S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and
T. miscellaneous herbicides including N,N-dimethyldiphenylacetamide (common name diphenamid), N-(1-naphthyl)phthalamic acid (common name naptalam) and 3-amino-1,2,4,-triazole.
Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);
V. organoarsenical herbicides such as monosodium methanearsonate (common name MSMA); and
W. amino acid herbicides such as N-(phosphonomethyl)glycine (common name glyphosate) and its salts and esters.

The invention is now illustrated by, but in no way limited to, the following examples.

EXAMPLE 1

4,7-Dimethylindane (i) β-Chloropropionyl chloride (71.9 g, 566 mmole) was added to a mixture of aluminium chloride (75.5 g, 566 mmole) and ethylene dichloride (200 ml). To this mixture was added p-xylene (60.0 g, 566 mmole) and the solution was stirred at room temperature for 30 minutes, then poured into dilute hydrochloric acid. The organic layer was separated, washed with water and dried over anhydrous sodium sulfate. Evaporation of the solvent under reduced pressure gave 2-(2-chloropropionyl)-2,4-dimethylbenzene a yellowish oil, which was used immediately in the next step of the sequence.

(ii) The crude 2-(2-chloropropionyl)-1,4-dimethylbenzene was slowly added to concentrated sulfuric acid (400 ml), preheated to 105° C. The solution was then stirred at 105°-110° C. for 30 minutes. The cooled mixture was poured onto cracked ice and the precipitate collected to give 4,7-dimethylindan-1-one (59.4 g, 65.6%) as a pale solid, mp 70° C.

(iii) Zinc amalgam (prepared by mixing zinc dust (25.0 g), mercuric chloride (2.5 g), concentrated hydrochloric acid (3 ml) and water (50 ml) together for 5 minutes, then decanting the aqueous solution) was added to a mixture of 4,7-dimethylindan-1-one (25.0 g, 156 mmole), acetic acid (50 ml), water (50 ml) and concentrated hydrochloric acid (100 ml). The mixture was refluxed with vigorous stirring for 12 hours, then cooled, poured into water and extracted with diethyl ether. The ether extract was washed successively with water, dilute aqueous sodium bicarbonate solution and water. Then dried over anhydrous sodium sulfate and concentrated. Purification by column chromatography over silica gel (eluant hexane) gave 4,7-dimethylindane (18.5 g, 81.4%) as an oil.

The product was characterized by proton nuclear magnetic resonance spectroscopy and the spectroscopic data is recorded in Table 2.

EXAMPLE 2

The indane derivatives listed in Table 2 were prepared following essentially the same procedure as that described in Example 1. Each of the products was characterized by proton nuclear magnetic resonance spectroscopy and spectroscopic data is recorded in Table 2 below.

TABLE 2

Indane Precursors to the Compounds of Formula I

| Indane derivatives | Appearance | Proton Chemical Shift δ in ppm (CDCl$_3$) |
|---|---|---|
| 4,7-(CH$_3$) | Colourless oil | 1.90–2.20(8H, m); 2.80 (4H, t); 6.80(2H, s). |
| 5-Br-4,6-(CH$_3$)$_2$ | Yellow oil | 1.90–2.30(2H, m); 2.32 (3H, s); 2.36(3H, s); 2.81(4H, t); 6.94(1H, s) |
| 4,6,7-(CH$_3$)$_3$ | Colourless solid mp <50° C. | 1.90–2.23(11H, m); 2.80 (4H, m); 6.75(1H, s). |
| 7-Br-4,6(CH$_3$)$_2$ | Colourless solid mp <50° C. | 1.90–2.20(5H, m); 2.30 (3H, s); 2.80–3.00 (4H, m); 6.85(1H, s). |
| 4,5,6-(CH$_3$)$_3$ | Colourless oil | 1.90–2.25(11H, m); 2.73–3.01(4H, m); 6.91 (1H, s). |
| 5-Br-4,7-(CH$_3$)$_2$ | Colourless oil | 1.90–2.20(5H, m); 2.27 (3H, s); 3.30–4.00(4H, m); 7.15(1H, s). |
| 5-C$_2$H$_5$-4,7-(CH$_3$)$_2$ | Colourless oil | 1.15(3H, t); 1.90–2.20 (8H, m); 2.60(2H, q); 2.70–2.95(4H, m); 6.73 (1H, s). |
| 4-Cl-5,7-(CH$_3$)$_2$ | Yellow oil | 1.82–2.38(8H, m); 2.90 (4H, m); 6.77(1H, s). |
| 4-Cl-6,7-(CH$_3$)$_2$ | Colourless oil | 1.85–2.33(8H, m); 2.68–3.00 (4H, m); 6.88(1H, s). |
| 5-Cl-4,7-(CH$_3$)$_2$ | White solid, mp <50° C. | 1.90–2.30(8H, m); 2.68–3.00 (4H, m); 6.93(1H, s). |
| 5-Cl-4,6-(CH$_3$)$_2$ | Colourless oil | 1.82–2.22(2H, m); 2.28 (3H, s); 2.32(3H, s); 2.83 (4H, t); 6.92(1H, s). |
| 5-F-4,6-(CH$_3$)$_2$ | Colourless oil | 1.90–2.20(8H, m); 2.60–2.90 (4H, m); 6.80(1H, d). |
| 5-CH$_2$CH$_2$CH$_2$-6 | Colourless oil | 2.05(4H, m); 2.85(8H, m); 7.05(2H, s). |
| 4-CH$_3$-5-CH$_2$CH$_2$-6 | Colourless oil | 2.05(7H, m); 2.85(8H, m); 6.95(1H, s). |

EXAMPLE 3

2,2,4,7-Tetramethylindane 4,7-Dimethylindan-1-one (6.00 g, 38 mmole) (see Example 1, parts (i) and (ii)) was dissolved in dimethylformamide (50 ml) and 60% sodium hydride (3.34 g; 76 mmole) was added portionwise over a period of 10 minutes. The mixture was allowed to stir for a further 10 minutes, then methyl iodide (25 ml) was added portionwise and stirring continued at room temperature overnight. The mixture was poured onto cracked ice and extracted with diethyl ether. The ether extract was washed with water, dried over anhydrous sodium sulfate and evaporated under reduced pressure to give a dark oil. Treatment of the oil with zinc amalgam, as outlined in Example 1, part (iii), gave a colourless oil, which was purified by column chromatography over silica gel (eluant hexane) to give 2,2,4,7-tetramethylindane (5.35 g, 80.9%). The product was characterized by proton nuclear magnetic resonance spectroscopy and the spectroscopic data is recorded in Table 3.

EXAMPLE 4

The indane derivatives listed in Table 3 were prepared following essentially the same procedure as that described in Example 3. Each of the products were characterized by proton nuclear magnetic resonance spectroscopy and the spectroscopic data is recorded in Table 3 below.

TABLE 3

Indane Precursors to the Compounds of Formula I

| Indane derivatives | Appearance | Proton Chemical Shift δ in ppm (CDCl$_3$) |
|---|---|---|
| 2,2-(CH$_3$)$_2$-6-Br | Colourless oil | 1.14(6H, s); 2.65(4H, d); 6.80–7.30(3H, m). |
| 2,2,4,5,6-(CH$_3$)$_5$ | Colourless oil | 1.13(6H, s); 2.13(6H, s); |

TABLE 3-continued

Indane Precursors to the Compounds of Formula I

| Indane derivatives | Appearance | Proton Chemical Shift δ in ppm (CDCl₃) |
|---|---|---|
| | | 2.22(3H, s); 2.62(4H, m); 6.80(1H, s). |
| 2,2,4,5,7-(CH₃)₅ | Pale yellow oil | 1.15(6H, s); 2.10(3H, s); 2.15(3H, s); 2.23(3H, s); 2.68(4H, m); 6.70(1H, s). |
| 2,2,4,7-(CH₃)₄ | Pale yellow oil | 1.15(6H, s); 2.17(6H, s); 2.65(4H, s); 6.84(1H, s). |

EXAMPLE 5

This example details the preparation of the indanes, which were prepared by methods directly analogous to those described in the literature.

METHOD A

The indanes were prepared following the general method described by T F Wood and J Angiolini (Tetrahedron Letters, 1963, 1) and also by E J Eisenbraun et al (Journal of Organic Chemistry, 31, 2716, 1966). Each of the products was characterized by proton nuclear magnetic resonance spectroscopy and the spectroscopy data is recorded in Table 4 below.

METHOD B (i) The indanones were prepared following the general method described by L I Smith et al (Journal of the American Chemical Society, 73, 3843, 1951).

(ii) The indanes were prepared from the corresponding indanones following the general method described by W E Parham et al (Journal of the American Society, 78, 1440, 1956).

Each of the products was characterized by proton nuclear magnetic resonance spectroscopy and the spectroscopic data is recorded in Table 4 below.

METHOD C (i) 3-Phenylpropionic acids were prepared following the general method described by C Kaiser et al (Journal of Medicinal Chemistry, 23(5), 506, 1980).

(ii) The indanones were prepared from the appropriate 3-phenylpropionic acids following the general method described by J Koo (Journal of the American Chemical Society, 75, 1819, 1953).

(iii) The indanes were prepared from the corresponding indanones following essentially the same procedure as that described in Example 1, part (iii).

Each of the products was characterized by proton nuclear magnetic resonance spectroscopy and the spectroscopic data is recorded in Table 4 below.

TABLE 4

Indane Precursors to the Compounds of Formula I

| Indane Derivatives | Method | Appearance | Proton Chemical Shift δ in ppm (CDCl₃) |
|---|---|---|---|
| 3,3,4,5,7-(CH₃)₅ | A | Colourless oil | 1.35(6H, s); 1.84(2H, t); 2.12-2.26(6H, m); 2.70 (2H, t); 6.80(1H, s). |
| 2,3,3,4,5,7-(CH₃)₆ | A | Colourless oil | 0.80-1.10(7H, m); 1.40 (3H, s); 2.21(3H, s); 2.23(3H, s); 2.25(3H, s); 2.75(2H, d); 6.80(1H, s). |
| 1,1,4,5,6-(CH₃)₅ | A | Colourless oil | 0.90(2H, m); 1.24(6H, s); 2.18(6H, s); 2.25(3H, s); 2.90(2H, m); 6.80(1H, s). |
| 2-CH₃-5-Br | C | Colourless oil | 1.10(3H, d); 1.20(1H, m); 2.60-3.00(4H, m); 7.00-7.40(3H, m). |
| 2,4,5,7-(CH₃)₄ | B | Colourless oil | 1.17(4H, m); 2.10(3H, s); 2.15(3H, s); 2.20(3H, s); 2.80-3.10(4H, m); 6.77 (1H, s). |
| 1,4,5,7-(CH₃)₄ | B | Colourless oil | 1.10(3H, d); 1.50(2H, m); 2.10(3H, s); 2.19(6H, s); 2.60-2.90(2H, m); 3.10-3.30(1H, m); 6.70(1H, s). |
| 2,4,5,6-(CH₃)₄ | B | Colourless oil | 1.17(4H, m); 1.80(6H, s); 1.20(3H, s); 2.80-3.10 (4H, m); 6.83(1H, s). |
| 3,4,5,6-(CH₃)₄ | B | Colourless oil | 1.10(5H, m); 2.10(3H, s); 2.20(6H, s); 2.60-3.50 (4H, m); 6.83(1H, s). |

EXAMPLE 6

This Example details the preparation of the indanecarboxaldehydes of formula V which were used in the preparation of the compounds of the invention of formula I.

METHOD A

The indanecarboxaldehydes were prepared from the corresponding aminoindane following the general method described by W F Beech et al (Journal of the Chemical Society, 1954, page 1297) and S D Jolad et al (Organic Synthesis, Vol 5, page 139). The products were characterized by proton magnetic resonance spectroscopy and the details are recorded in Table 5, below.

METHOD B

The indanecarboxaldehydes were prepared from the corresponding bromoindane following the general method described by G A Olah et al (Angew. Chem. Int. Ed. 20(10), 878, 1981). The products were characterized by proton magnetic resonance spectroscopy and the details are recorded in Table 5, below.

METHOD C:

The indanecarboxaldehydes were prepared by direct formylation of the indane ring following the general method described by A Rieche et al (Organic Synthesis, Vol 5, page 49). The products were characterized by proton magnetic resonance spectroscopy and the details are recorded in Table 5, below.

TABLE 5

Indanecarboxaldehyde Precursors to the Compounds of Formula I

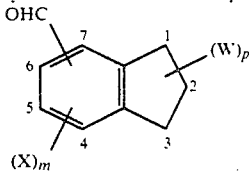

| Indane-carboxaldehyde (X)$_m$ + (W)$_p$ | CHO | Method | Appearance | Proton Chemical Shift δ in ppm (CDCl$_3$) |
|---|---|---|---|---|
| H | 5- | A | Yellow oil | 1.20(2H, m); 3.00(4H. m); 7.00–7.80(3H, m); 9.80(1H. s). |
| 4,7-(CH$_3$)$_2$ | 5- | C | Pale yellow solid mp <50° C. | 1.90–2.20(5H. m); 2.55 (3H, s); 2.70–3.00(4H. m); 7.40(1H, s); 10.20 (1H. s). |
| 4,6-(CH$_3$)$_2$ | 5- | B | Yellow oil | Not recorded |
| 4,6,7-(CH$_3$)$_3$ | 5- | C | Pale yellow solid mp 107° C. | 1.80–2.40(5H, m); 2.42 (6H, s); 2.90(4H. m); 10.60(1H. s). |
| 7-Br-4,6-(CH$_3$)$_2$ | 5- | C | Yellow solid mp 115° C. | 1.90–2.20(5H. m); 2.55 (3H, s); 2.70–3.00(4H. m); 10.50(1H. s). |
| 4,6-(CH$_3$)$_2$ | 7- | B | Brown oil | 1.85–2.42(5H. m); 2.60 (3H, s); 2.77(2H. t); 3.29(2H. t); 6.87(1H. s); 10.51(1H. s). |
| 4,5,6-(CH$_3$)$_3$ | 7- | C | Brown solid mp <50° C. | 1.90–2.20(8H. m); 2.60(3H, s); 2.80(2H. t); 3.20(2H. t); 10.60 (1H. s). |
| 5-Br-4,7-(CH$_3$)$_2$ | 6 | C | Yellow solid, mp 115° C. | 1.90–2.20(2H, m); 2.35 (3H, s); 2.40(3H. s); 2.75–3.00(4H, m); 10.22 (1H. s). |
| 4,7-(CH$_3$)$_2$-5-C$_2$H$_5$ | 6 | C | Colourless mp <50° C. | 1.20(3H. t); 1.90–2.20 (2H. m); 2.20(3H. s); 2.40(3H. s); 2.75–3.00 (6H. m); 10.60(1H. s). |
| 4-Cl-5,7-(CH$_3$)$_2$ | 6 | C | Oil | 1.85–2.50(5H. m); 2.60 (3H, s); 2.72–3.20 (4H. m); 10.48(1H. s). |
| 4-Cl-6,7-(CH$_3$)$_2$ | 5 | C | Bone solid, mp 108–110° C. | 1.80–2.52(8H. m); 2.75–3.16(4H. m); 10.55 (1H. s). |
| 5-Cl-4,7-(CH$_3$)$_2$ | 6 | C | Yellow solid, mp 124° C. | 1.97–2.40(8H. m); 2.70–2.90(4H. m); 10.50(1H. s). |
| 5-F-4,6-(CH$_3$)$_2$ | 7 | C | Brown oil | 2.20(3H, d); 2.50(3H. d); 2.80(2H. t); 3.22(2H. t); 10.40(1H. s). |
| 2-CH$_3$ | 5 | B | Brown oil | 1.10(3H, d); 1.50(1H. m); 2.50(2H, m); 3.00(2H, m); 7.20(3H, m); 9.90(1H, s). |
| 2,2-(CH$_3$)$_2$ | 5 | B | Brown oil | 1.10(6H, s); 2.50(2H, s); 3.01(2H, s); 7.30(3H, m); 9.90(1H, s). |
| 3,3,4,5,7-(CH$_3$)$_5$ | 6 | C | Yellow oil | 1.40(6H, s); 1.90(2H, t); 2.20(3H, s); 2.40(6H, s); 2.80(2H, t); 10.60(1H, s) |
| 2,3,3,4,5,7-(CH$_3$)$_6$ | 6 | C | Brown oil | 1.00(6H, m); 1.40(3H, s); 2.00–2.60(11H, m); 2.90 (1H, m); 10.78(1H, s). |
| 2,4,5,7-(CH$_3$)$_4$ | 6 | C | Yellow solid, mp 50° C. | 1.12(3H, d); 2.10–2.60 (12H, m); 2.80–3.20 (2H, m); 10.60(1H, s). |
| 1,4,5,7-(CH$_3$)$_4$ | 6 | C | Yellow oil | 1.10(3H, d); 1.80–2.20 (2H, m); 2.20(3H, s); 2.41(6H, s); 2.80–3.00 (2H, m); 3.40(1H, m); 10.50(1H, s). |
| 2,2,4,5,6-(CH$_3$)$_5$ | 7 | C | Brown oil | 1.10(6H, s); 2.20(6H, s); 2.55(3H, s); 2.62(2H, s); 3.05(2H, s); 10.20(1H, s) |
| 1,1,4,5,6-(CH$_3$)$_5$ | 7 | C | Yellow | 1.40(6H, s); 1.90(2H, t); |

TABLE 5-continued
Indanecarboxaldehyde Precursors to the Compounds of Formula I

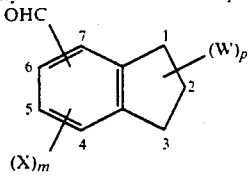

| Indane-carboxaldehyde (X)$_m$ + (W)$_p$ | CHO | Method | Appearance | Proton Chemical Shift δ in ppm (CDCl$_3$) |
|---|---|---|---|---|
| | | | oil | 2.19(3H, s); 2.22(3H, s); 2.40(3H, s); 2.80(2H, t); 10.60(1H, s). |
| 2,4,5,6-(CH$_3$)$_4$ | 7 | C | Brown oil | 1.10(3H, d); 2.20(6H, s); 2.50(3H, s); 2.20–2.60 (1H, m); 2.80–3.00(2H, m); 3.40(2H, m); 10.46 (1H, s). |
| 3,4,5,6-(CH$_3$)$_4$ | 7 | C | Yellow oil | 1.10(3H, d); 1.90(2H, m); 2.20(3H, s); 2.38(6H, s); 2.80(3H, m); 10.65 (1H, s). |
| 2,2,4,5,7-(CH$_3$)$_5$ | 6 | C | Yellow solid. mp <50° C. | 1.25(6H, s); 2.13(3H, s); 2.37(3H, s); 2.40(3H, s); 2.70(4H, s); 10.60(1H, s) |
| 2,2,4,7-(CH$_3$)$_4$ | 5 | C | Yellow oil | 1.20(6H, s); 2.23(3H, s); 2.45(3H, s); 2.70(4H, s); 7.40(1H, s); 10.60(1H, s) |
| 5-CH$_2$CH$_2$CH$_2$-6 | 4 | C | Yellow solid | 2.00–2.20(4H, m); 2.90 (4H, t); 3.20(4H, t); 7.48(1H, s); 10.38(1H, s) |
| 5-CH$_2$CH$_2$CH$_2$-6-7-CH$_3$ | 4 | C | Yellow solid. mp <50° C. | 2.00–2.20(7H, m); 2.80 (4H, t); 3.25(4H, t); 10.20(1H, s). |

EXAMPLE 7

This example details the preparation of the tetrahydronaphthalenecarboxaldehydes and the benzosuberanecarboxaldehydes of formula V, which were used in the preparation of the compounds of the invention of formula I. The carboxaldehydes were prepared following essentially the same procedures as that described in Example 6. The products were characterized by proton magnetic resonance spectroscopy and the spectroscopic details are recorded in Table 6, below.

TABLE 6
Tetrahydronaphthalenecarboxaldehyde and Benzosuberane-carboxaldehyde Precursors to the Compounds of Formula I

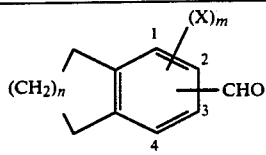

| (X)$_m$ | CHO | n | Method | Appearance | Proton Chemical Shift δ in ppm (CDCl$_3$) |
|---|---|---|---|---|---|
| 2,3,4-(CH$_3$)$_3$ | 1 | 2 | C | Yellow solid, mp 51° C. | 1.60–1.80(4H, m); 2.20 (6H, s); 2.40(3H, s); 3.60(2H, m); 4.00(2H, m); 10.55(1H, s). |
| 2,3,4-(CH$_3$)$_3$ | 1 | 3 | C | Yellow solid, mp 50° C. | 1.40–1.60(6H, m); 2.20 (3H, s); 2.30(3H, s); 2.40(3H, s); 2.80–3.00 (4H, m); 10.50(1H, s). |
| 2-OCH$_3$-3,4-(CH$_3$)$_2$ | 1 | 2 | C | Brown oil | 1.75(4H, m); 2.20(6H, s); 2.60(2H, m); 3.00(2H, m); 3.80(3H, s); 10.50(1H, s) |

EXAMPLE 8

2-[1-(Ethoxyimino)propyl]-3-hydroxy-5-(5-indanyl)cyclohex-2-en-1-one (1)

(i) An aqueous solution of 10% sodium hydroxide (50–70 ml) was added dropwise over a period of 5 minutes to a suspension of indane-5-carboxaldehyde (18.50 g; 127 mmole) in acetone (50 ml) and water (50 ml). The mixture was stirred at a temperature of 65° C. for a period of 1½ hours and then extracted with dichloromethane (200 ml). The organic extract was washed several times with water, dried over anhydrous sodium sulphate, and the solvent was removed under reduced pressure using a rotary evaporator to give 1-(5-indanyl)-but-1-en-3-one (19.25 g; 81%) as a viscous oil.

Proton magnetic resonance spectrum (CDCl$_3$; δ in ppm): 2.05 (2H,m); 2.35 (3H,s); 2.90 (4H, m); 6.62 (1H, d); 7.10–7.60 (4H, m).

(ii) Diethyl malonate (17.5 g; 110 mmole) was added to a solution of sodium metal (1.91 g; 83 mmole) in anhydrous absolute ethanol (50 ml) and the mixture was heated to reflux temperature. A mixture of 1-(5-indanyl)but-1-en-3-one (19.25 g; 103 mmole) in anhydrous absolute ethanol (50 ml) was added over a period of two minutes and the mixture was heated under reflux for a period of 2 hours. An aqueous solution of sodium hydroxide (30% solution, 50 ml) was added and the mixture was heated under reflux for a further 1½ hours. The solution was poured into water (200 ml) and the aqueous mixture was extracted twice with ethyl acetate (2×100 ml). The aqueous phase was acidified with concentrated hydrochloric acid and warmed gently until the evolution of carbon dioxide ceased. The aqueous mixture was extracted with ethyl acetate, dried over anhydrous sodium sulphate, and the solvent was removed by evaporation under reduced pressure using a rotary evaporator. The product, 3-hydroxy-5-(5-indanyl)cyclohex-2-en-1-one, was obtained as a white solid (18.70 g; 79.6%), mp 198° C.

Proton magnetic resonance spectrum (d$_6$-dimethylsulfoxide; δ in ppm): 1.80–3.80 (11H, m); 5.20 (1H, s); 7.00–7.20 (3H, m); 11.8 (1H, broad s).

(iii) METHOD (A)

A mixture of 3-hydroxy-5-(5-indanyl)cyclohex-2-en-1-one (5.0 g; 22 mmole) in dichloromethane (100 ml) and pyridine (1.74 g; 22 mmole) was stirred at room temperature whilst propionyl chloride (1.92 g; 22 mmole) was added dropwise over a period of two minutes. Stirring was continued for 1 hour after which the organic solution was washed with water (2×100 ml), dried over anhydrous sodium sulphate, and the solvent was removed under reduced pressure using a rotary evaporator. The resulting brown oil was immediately dissolved in 1,2-dichloroethane (50 ml) and added dropwise to a mixture of aluminium trichloride (5.85 g; 44 mmole) in 1,2-dichloroethane (50 ml) over 30 min at such a rate that the temperature did not exceed 30° C. After stirring for 30 min at room temperature, the solution was poured into 100 ml of a 1:1 mixture of concentrated hydrochloric acid and water. The organic solution was washed with water (2×200 ml), dried over anhydrous sodium sulphate and the solvent was removed under reduced pressure using a rotary evaporator. The resulting yellow oil was purified by chromatography over silica gel (eluant dichloromethane) to give 3-hydroxy-5-(5-indanyl)-2-propionylcyclohex-2-en-1-one, (1.71 g; 27%) as a yellow solid, mp 98° C.

Proton magnetic resonance spectrum (CDCl$_3$; δ in ppm): 1.10 (3H, t); 2.00 (2H, m); 2.50–3.40 (11H, m); 7.00–7.40 (3H, m); 18.0 (1H, s).

(iii) METHOD (b)

3-Hydroxy-5-(5-indanyl)cyclohex-2-en-1-one (4.0 g; 18 mmole) was dissolved in a mixture of propionic acid (4 ml) and propionic anhydride (4 ml) at 130° C. under nitrogen. To the resulting clear solution was added 8 drops of trifluoromethyl sulphonic acid and the mixture was allowed to stir at 130° C. under nitrogen for a further 1½ hours. The mixture was poured into water (500 ml) and stirred until all the anhydride had reacted (approx 30 min). The resulting solid was filtered off, pressed dry at the pump and then dissolved in dichloromethane and purified by column chromatography over silica gel (eluant dichloromethane) to give 3-hydroxy-5-(5-indanyl)-2-propionylcyclohex-2-en-1-one (1.88 g; 37%), mp 98° C.

(iii) METHOD (c)

3-Hydroxy-5-(5-indanyl)cyclohex-2-en-1-one (4.0 g; 18.0 mmole) was added to a solution of sodium hydride (0.80 g of 60% w/w; 20.0 mmole) in dry dimethylformamide (50 ml) under an atmosphere of nitrogen. After 15 minutes propionic anhydride (2.6 g; 20.0 mmole) was added and the mixture was heated at 110°–120° C. for 2 hours. It was then poured into water (300 ml) and extracted with diethyl ether (2×100 ml). The ether extracts were dried over anhydrous sodium sulfate and then evaporated under reduced pressure to give a yellow oil. Purification by column chromatography over silica gel (eluent dichloromethane) gave 3-hydroxy-5-(5-indanyl)-2-propionylcyclohex-2-en-1-one (2.76 g; 54%) as a yellow solid, mp 98° C.

(iv) Ethoxyamine hydrochloride (0.42 g; 4.1 mmole) and then aqueous 1% sodium hydroxide (17.0 ml) were added to a solution of 3-hydroxy-5-(5-indanyl)-2-propionylcyclohex-2-en-one (1.10 g; 3.87 mmole) in anhydrous absolute ethanol (200 ml). The mixture was stirred at room temperature for a period of 4 hours and then the ethanol was removed by evaporation under reduced pressure using a rotary evaporator. The residue was treated with dichloromethane and the organic phase was washed twice with dilute aqueous hydrochloric acid and twice with water. The organic phase was dried over anhydrous sodium sulphate and the solvent was removed by evaporation under reduced pressure to give the product, 2-[1-(ethoxyimino)-propyl]-3-hydroxy-5-(5-indanyl)-cyclohex-2-en-1-one (1.20 g; 94.8%) as a pale yellow oil.

The product was characterized by proton nuclear magnetic resonance spectroscopy and the spectroscopic data is recorded in Table 9, Example 30.

EXAMPLE 9

Compounds No 8, 9, 10, 11, 12, 13, 14, 15, 16, 19, 20, 21, 22, 26, 27, 46, 47, 48, 52, 54 and 57 (see Tables 1a–1d) were prepared from the appropriate aldehyde derivative (see Examples 6 and 7) following essentially the same procedure as that outlined in Example 8. Each of the products was characterized by proton nuclear magnetic resonance spectroscopy and the spectroscopic data is recorded in Table 9, Example 30.

EXAMPLE 10

2-[1-(Ethoxyimino)butyl]-3-hydroxy-5-(5-indanyl)cyclohex-2-en-1-one (5)

(i) 2-Butyryl-3-hydroxy-5-(5-indanyl)cyclohex-2-en-1-one, a yellow solid mp 92° C., was prepared from 3-hydroxy-5-(5-indanyl)cyclohex-2-en-1-one and butyric anhydride following essentially the same procedure as that described in Example 8, part (iii) Method (b) and Method (c).

(ii) 2-[1-(Ethoxyimino)butyl]-3-hydroxy-5-(5-indanyl)cyclohex-2-en-1-one, a yellow oil, was prepared from 2-butyryl-3-hydroxy-5-(5-indanyl)cyclohex-2-en-1-one and ethoxyamine hydrochloride in 86.1% yield following essentially the same procedure as that described in Example 8 part (iv).

The product was characterized by proton nuclear magnetic resonance spectroscopy and the spectroscopic data is recorded in Table 9 Example 30.

EXAMPLE 11

Compounds No 23, 24, 34, 49, 50, 51, 53, 55, 56, 58, 59, 60 and 61 (see Tables 1a and 1b) were prepared from the appropriate 3-hydroxy-5-(substituted indanyl)cyclohex-2-en-1-one (see Example 28), butyric anhydride and ethoxyamine hydrochloride following essentially the same procedure as that described in Example 10. Each of the products was characterized by proton nuclear magnetic resonance spectroscopy and the spectroscopic data is recorded in Table 9, Example 30.

EXAMPLE 12

Compounds No 4, 6, 39 and 44 (see Tables 1a and 1b) were prepared from the appropriate 2-alkanoyl-3-hydroxy-5-(substituted indanyl)cyclohex-2-en-1-one (see Example 29) and the appropriate hydroxyamine hydrochloride derivative following essentially the same procedure as that described in Example 8, part (iv). Each of the products was characterized by proton nuclear magnetic resonance spectroscopy and the spectroscopic data is recorded in Table 9, Example 30.

EXAMPLE 13

Sodium salt of 2-[1-(ethoxyimino)propyl]-3-hydroxy-5-(5-indanyl)cyclohex-2-en-1-one (2)

2-[1-(Ethoxyimino)propyl]-3-hydroxy-5-(5-indanyl)-cyclohex-2-en-1-one, (0.31 g; 0.95 mmole) was dissolved in acetone (20 ml) and aqueous 1% sodium hydroxide (3.8 ml) was added in one portion. The mixture was allowed to stir at room temperature for 10 min and then the acetone was removed under reduced pressure on a rotary evaporator. Toluene (50 ml) was added and was similarly removed by distillation. A further two aliquots of toluene were added and then distilled off to give 2-[1-(ethoxyimino)propyl]-3-hydroxy-5-(5-indanyl)cyclohex-2-en-1-one sodium salt as a pale yellow solid, mp<250° C.

EXAMPLE 14

Compounds No 31, 33 and 35 were prepared from compounds No 61, 60 and 34 (see Table 1b) and sodium hydroxide following essentially the same procedure as that described in Example 13. The products may be identified by their melting points which are recorded in Table 9, Example 30.

EXAMPLE 15

3-Benzoyl-2-[1-(ethoxyimino)propyl]-5-(5-indanyl)cyclohex-2-en-1-one (3)

The sodium salt of 2-[1-(ethoxyimino)propyl]-3-hydroxy-5-(5-indanyl)cyclohex-2-en-1-one (0.95 mmole) was dissolved in acetone (50 ml) and benzoyl chloride (0.13 g; 0.95 mmole) was added dropwise over a period of 2 minutes. The mixture was stirred at room temperature for 5 minutes, then filtered and evaporated under reduced pressure to give 3-benzoyl-2-[1-(ethoxyimino)propyl]-5-(5-indanyl)cyclohex-2-en-1-one (0.31 g; 75.7%) as a yellow oil.

The product was characterized by proton nuclear magnetic resonance spectroscopy and the spectroscopic data is recorded in Table 9, Example 30.

EXAMPLE 16

Compounds Nos 32, 37, 38 and 42 were prepared from the sodium salt of 2-[1-(ethoxyimino)butyl]-3-hydroxy-5-(5,6,7-trimethyl-4-indanyl)cyclohex-2-en-1-one (31) and the appropriate acid chloride following essentially the same procedure as that described in Example 15. Each of the products was characterized by proton nuclear magnetic resonance spectroscopy and the spectroscopic data is recorded in Table 9, Example 30.

EXAMPLE 17

Copper salt of 2-[1-(ethoxyimino)butyl]-3-hydroxy-5-(5,6,7-trimethyl-4-indanyl)cyclohex-2-en-1-one (40)

2-[1(Ethoxyimino)butyl]-3-hydroxy-5-(5,6,7-trimethyl-4-indanyl)cyclohex-2-en-1-one (61), (500 mg, 1.3 mmole) in diethyl ether (50 ml) was shaken with a saturated aqueous cupric acetate solution (50 ml). The mixture was then evaporated to dryness under reduced pressure. The solid residue was washed successively with hot water, cooled water and diethyl ether, then dried to give the copper salt of 2-[1-(ethoxyimino)-butyl]-3-hydroxy-5-(5,6,7-trimethyl-4-indanylcyclohex-2-en-1-one (450 mg, 84%) as a pale green solid, mp 212° C.

EXAMPLE 18

Nickel salt of 2-[1-(ethoxyimino)butyl]-2-hydroxy-5-(5,6,7-trimethyl-4-indanyl)cyclohex-2-en-1-one (41)

Compound No 41 was prepared from compound No 61 following an analogous procedure to that described in Example 17. The product was obtained as a solid and its melting point is recorded in Table 9, Example 30.

EXAMPLE 19

Lithium salt of 2-[1-(ethoxyimino)butyl]-3-hydroxy-5-(5,6,7-trimethyl-4-indanyl)cyclohex-2-en-1-one (36)

To a solution of 2-[1-(ethoxyimino)butyl]-3-hydroxy-5-(5,6,7-trimethyl-4-indanyl)cyclohex-2-en-1-one (61), (0.50 g; 1.3 mmole) in methanol (30 ml) was added a solution of lithium metal (9.0 mg, 1.3 mmole) dissolved in methanol (2 ml). The mixture was stirred for 15 minutes at room temperature and then evaporated to dryness under reduced pressure, to give the lithium salt of 2-[1-(ethoxyimino)butyl]-3-hydroxy-5-(5,6,7-trimethyl-4-indanyl)cyclohex-2-en-1-one (0.40 g; 78.0%) as a colourless solid, mp<250° C.

EXAMPLE 20

Tetrabutylammonium salt of 2-[1-ethoxyimino)butyl]-3-hydroxy-5-(5,6,7-trimethyl-4-indanyl)cyclohex-2-en-1-one (43)

To a solution of 2-[1-(ethoxyimino)butyl]-3-hydroxy-5-(5,6,7-trimethyl-4-indanyl)cyclohex-2-en-1-one (0.63 g; 1.6 mmole) in methanol (5 ml) was added a 25% methanolic solution of tetra-n-butyl ammonium hydroxide (2.0 ml). The mixture was kept at room temperature for 3 hours and then evaporated to dryness under reduced pressure using a rotary evaporator. The residue was taken up in dichloromethane (15 ml) and water (15 ml). The layers were separated and the organic layer washed with water (2×10 ml), dried over anhydrous sodium sulfate and evaporated under reduced pressure to afford the tetrabutylammonium salt of 2-[1-(ethoxyimino)butyl]-3-hydroxy-5-(5,6,7-trimethyl-4-indanyl)-cyclohex-2-en-1-one (0.56 g) as a yellow oil. The product was characterized by proton nuclear magnetic resonance spectroscopy and the spectroscopic data is reported in Table 9, Example 30.

EXAMPLE 21

5-(4,6-Dimethyl-7-N,N-dimethylsulfamoyl-5-indanyl)-2-[1-(ethoxyimino)propyl]-3-hydroxy-cyclohex-2-en-1-one (17)

(i) 5-(4,6-Dimethyl-5-indanyl)-2-propionylcyclohex-2-en-1-one (1.55 g; 4.8 mmole) in dichloromethane (12 ml) was cooled to 0° C. and chlorosulfonic acid (5.5 ml) was added dropwise. The temperature was maintained at 0° C. for a further 30 minutes, after which the mixture was allowed to warm to room temperature. The mixture was poured onto cracked ice and the organic layer separated, dried over anhydrous magnesium sulfate and evaporated to give 5-(7-chlorosulfonyl-4,6-dimethyl-5- indanyl)-3-hydroxy-2-propionylcyclohex-2-en-1-one (1.60 g; 81.0%) as a brown solid, which was used without further purification.

(ii) To a solution of water (35 ml) and 33% ethanolic dimethylamine (35 ml) at 0° C. was added 5-(7-chlorosulfonyl-4,6-dimethyl-5-indanyl)-3-hydroxy-2-propionylcyclohex-2-en-1-one (1.60 g; 3.9 mmole). The reaction was stirred at 0° C. for 30 minutes and then allowed to come to room temperature. The mixture was acidified with dilute hydrochloric acid, extracted with dichloromethane, dried over anhydrous magnesium sulfate and evaporated under reduced pressure to give 5-(4,6-dimethyl-7-N,N-dimethylsulfamoyl-5-indanyl)-3-hydroxy-2-propionylcyclohex-2-en-1-one (1.40 g; 86.0%) as a yellow oil. The product was characterized by proton nuclear magnetic resonance spectroscopy and the spectroscopic data is recorded in Table 8, Example 29.

(iii) 5-(4,6-Dimethyl-7-N,N-dimethylaminosulfamoyl-5-indanyl)-2-[1-(ethoxyimino)propyl]-3-hydroxycyclohex-2-en-1-one (17) was prepared from 5-(4,6-dimethyl-7-N,N-dimethylaminosulfamoyl-5-indanyl)-3-hydroxy-2-propionylcyclohex-2-en-1-one, following an analogous procedure to that described in Example 8, part (iv). The product was characterized by proton nuclear magnetic resonance spectroscopy and the spectroscopic data is recorded in Table 9, Example 30.

EXAMPLE 22

Compound No 18 was prepared from 5-(4,7-dimethyl-5-indanyl)-3-hydroxy-2-propionylcyclohex-2-en-1-one (see Example 29) by essentially the same procedure as that outlined in Example 21. The product was characterized by proton nuclear magnetic resonance spectroscopy and the spectroscopic data is recorded in Table 9, Example 30.

EXAMPLE 23

5-(6-Chloro-4,7-dimethyl-5-indanyl)-2-[1-(ethoxyimino)benzyl]-3-hydroxycyclohex-2-en-1-one (25)

(i) 5-(6-Chloro-4,7-dimethyl-5-indanyl)-3-hydroxycyclohex-2-en-1-one (see Example 28) (1.40 g; 4.8 mmole) was dissolved in ethanol (50 ml) and sodium bicarbonate (0.45 g; 5.3 mmole) dissolved in water (20 ml) was added. The mixture was stirred until the evolution of carbon dioxide had ceased and then the solvent was removed under reduced pressure. The dried solid was dissolved in dimethylformamide (50 ml) and heated to 110° C. Benzoic anhydride (1.19 g; 5.3 mmole) dissolved in dimethylformide (10 ml) was added and the mixture was stirred at 110° C. for 2 hours. The solvent was removed under reduced pressure and the residue was purified by column chromatography over silica gel (eluant dichloromethane) to give 2-benzoyl-5-(6-chloro-4,7-dimethyl-5-indanyl)-3-hydroxy-cyclohex-2-en-1-one (0.43 g; 23.0%) as a yellow oil. The product was characterized by proton nuclear magnetic resonance spectroscopy and the spectroscopic data is recorded in Table 8, Example 29.

(ii) 5-(6-Chloro-4,7-dimethyl-5-indanyl)-2-[1-(ethoxyimino)benzyl]-3-hydroxy-cyclohex-2-en-1-one and ethoxyamine hydrochloride following essentially the same procedure as that described in Example 8, part (iv). The product was characterized by proton nuclear magnetic resonance spectroscopy and the spectroscopic data is recorded in Table 9, Example 30.

EXAMPLE 24

Compound No 45 was prepared from 3-hydroxy-5-(5,6,7-trimethyl-4-indanyl)cyclohex-2-en-1-one (see Example 28) by an analogous method to that described in Example 23. The product was characterized by proton nuclear magnetic resonance spectroscopy and the spectroscopic data is recorded in Table 9, Example 30.

EXAMPLE 25

2-[1-(Ethoxyimino)propyl]-3-hydroxy-5-(5,6,7,8-tetrahydro-2-naphthyl)cyclohex-2-en-1-one (7)

(i) 1-(5,6,7,8-Tetrahydro-2-naphthyl)but-1-en-3-one, a yellow oil, was prepared from 5,6,7,8-tetrahydro-2-naphthaldehyde and acetone in 63% yield following essentially the same procedure as that described in Example 8, part (i).

Proton magentic resonance spectrum (CDCl$_3$; δ in ppm): 1.65 (4H m); 2.30 (3H, s); 2.70 (4H, m); 6.60 (1H, d); 7.00–7.30 (3H, m); 7.40 (1H, d).

(ii) 3-Hydroxy-5-(5,6,7,8-tetrahydro-2-naphthyl)cyclohex-2-en-1-one, a pale yellow solid mp 198° C., was prepared from 1-(5,6,7,8-tetrahydro-2-naphthyl)-but-1-en-3-one in 48.3% yield following essentially the same procedure as that described in Example 8 part (ii).

(iii) 3-Hydroxy-5-(5,6,7,8-tetrahydro-2-naphthyl)cyclohex-2-en-1-one (2.6 g; 11.0 mmole) was added to a solution of sodium hydride (0.47 g of 60% w/w; 12.0 mmole) in dry dimethylformamide (10 ml) under an atmosphere of nitrogen. The mixture was stirred under nitrogen until a solution had been obtained and propionic anhydride was added dropwise and the mixture was heated to 120° C. The mixture was stirred at 120° C. under nitrogen for a period of 2 hours and then the solvent was evaporated under reduced pressure. The mixture was treated with dichloromethane (20 ml) and the soluble portion of the residue was chromatrographed over silica gel (eluant dichloromethane) to give 3-hydroxy-2-propionyl-5-(5,6,7,8-tetrahydro-2-naphthyl)cyclohex-2-en-1-one (0.86 g; 26.2%) as a yellow solid, mp 87° C.

(iv) 2-[1-(Ethoxyimino)propyl]-3-hydroxy-5-(5,6,7,8-tetrahydro-2-naphthyl)cyclohex-2-en-1-one, a yellow oil, was prepared from 3-hydroxy-2-propionyl-5-(5,6,7,8-tetrahydro-2-naphthyl)cyclohex-2-en-1-one and ethoxyamine hydrochloride in 57.3% yield following essentially the same procedure as that described in Example 8 part (iv).

The product was characterized by proton nuclear magnetic resonance spectroscopy and the spectroscopic data is recorded in Table 9, Example 30.

EXAMPLE 26

Compounds No 27, 28 and 30 (see Table 1c) were prepared from the appropriate 3-hydroxy-5-(substituted 5,6,7,8-tetrahydro-1-naphthyl)cyclohex-2-en-1-one (see Example 28) and the appropriate carboxylic anhydride and ethoxyamine hydrochloride following essentially the same procedure as that described in Example 25. Each of the products was characterized by proton nuclear magnetic resonance spectroscopy and the spectroscopic data is recorded in Table 9, Example 30.

EXAMPLE 27

Compound No 29 (see Table 1e) was prepared from 3-hydroxy-5-(2,3,4-trimethyl-1-benzosuberanyl)cyclohex-2-en-1-one (see Example 28), propionic anhydride and ethoxyamine hydrochloride following essentially the same procedure as that described in Example 25. The product was characterized by proton nuclear magnetic resonance spectroscopy and the spectroscopic data is recorded in Table 9, Example 30.

EXAMPLE 28

The 5-arylcyclohexane-1,3-diones of formula IX used in the preparation of the compounds of formula I were prepared from the appropriate arylaldehyde derivative following essentially the same procedure as that described in Example 8 parts (i) and (ii).

The majority of the 5-arylcyclohexane-1,3-diones of formula IX were obtained as solids and were characterized by their nuclear magnetic resonance spectra. For convenience, proton nuclear magnetic resonance spectroscopic (pmr) data and/or melting point data is recorded in Table 7 below.

TABLE 7a

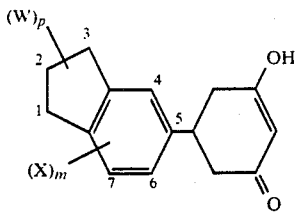

| $(X)_m + (W)_p$ | Appearance | Proton Chemical Shift δ in ppm ($D_6$-DMSO) |
|---|---|---|
| H | Pale yellow solid, mp 198° C. | 1.80-3.80(11H, m); 5.20 (1H, s); 7.00-7.20(3H, m); 11.80(1H, s). |
| 4,7-$(CH_3)_2$ | Yellow solid, mp 184° C. | 1.75-2.18(8H, m); 2.20-3.60(9H, m); 5.25(1H, s); 6.90(1H, s); 11.00(1H, s). |
| 4,6-$(CH_3)_2$ | Yellow solid | 2.00(2H, m); 2.12-2.20(6H, m); 2.20-3.40(8H, m); 3.95 (1H, m); 5.80(1H, s); 6.55 (1H, s); 11.00(1H, s). |
| 7-Br-4,6-$(CH_3)_2$ | Yellow solid | 2.00(2H, m); 2.20(3H, s); 2.40(3H, s); 2.40-3.45 (8H, m); 3.95(1H, m); 5.30 (1H, s); 11.00(1H, s). |
| 2,2,4,7-$(CH_3)_4$ | Colourless solid, mp 245° C. | Not recorded |
| 2,2,4,6,7-$(CH_3)_5$ | Yellow solid | 1.10(6H, s); 2.10(3H, s); 2.20(6H, s); 2.40-3.00 (8H, m); 3.70(1H, m); 5.27 (1H, s); 11.00(1H, s). |
| 2,2-$(CH_3)_2$ | Yellow solid, mp 170° C. | not recorded |
| 6-Br-4,7-$(CH_3)_2$ | Yellow solid | 2.00(2H, m); 2.20(3H, s); 2.30(3H, s); 2.38-3.40 (8H, m); 3.90(1H, m); 5.50 (1H, s); 11.10(1H, s). |
| 4,7-$(CH_3)_2$-6-$C_2H_5$ | Yellow solid, mp 254° C. | Not recorded |
| 7-Cl-4,6-$(CH_3)_2$ | Yellow solid | 1.75-4.10(17H, m); 5.28 (1H, s); 11.20(1H, s). |
| 4-Cl-6,7-$(CH_3)_2$ | Cream solid, mp 226-230° C. | Not recorded |
| 6-Cl-4,7-$(CH_3)_2$ | Cream solid, mp 227° C. | Not recorded |
| 2-$CH_3$ | Yellow solid, mp 204° C. | Not recorded |
| 1,1,4,6,7-$(CH_3)_5$ | Tan solid, mp >250° C. | Not recorded |
| 1,1,2,4,6,7-$(CH_3)_6$ | Cream solid, mp 270° C. | Not recorded |
| 3,4,6,7-$(CH_3)_4$ | Colourless solid, mp 232° C. | Not recorded |
| 2,4,6,7-$(CH_3)_4$ | Cream solid, mp 213° C. | Not recorded |

TABLE 7a-continued

| $(X)_m + (W)_p$ | Appearance | Proton Chemical Shift δ in ppm ($D_6$-DMSO) |
|---|---|---|
| 4,6,7-$(CH_3)_3$ | Yellow solid, mp 221° C. | 1.80-2.40(11H, m); 2.45-4.00(9H, m); 5.35(1H, s); 11.00(1H, s). |

TABLE 7b

| $(X)_m + (W)_p$ | Appearance | Proton Chemical Shift δ in ppm ($D_6$-DMSO) |
|---|---|---|
| 5,7-$(CH_3)_2$ | Yellow solid | 1.80-2.40(8H, m); 2.45-3.00(8H, m); 3.40(1H, m); 5.45(1H, s); 6.75(1H, s); 11.00(1H, s). |
| 5,6,7-$(CH_3)_3$ | Yellow solid, mp 179° C. | 1.80-2.20(11H, m); 2.20-3.00(4H, m); 3.40-3.80 (5H, m); 5.20(1H, s); 11.00 (1H, s). |
| 6-Cl-5,7-$(CH_3)_2$ | Yellow solid, mp 160° C. | Not recorded |
| 6-F-5,7-$(CH_3)_2$ | Colourless solid | Not recorded |
| 2,2,5,6,7-$(CH_3)_5$ | Colourless solid, mp 246° C. | Not recorded |
| 3,3,5,6,7-$(CH_3)_5$ | Yellow solid | 1.40(6H, s); 1.90(2H, t); 2.16(3H, s); 2.19(3H, s); 2.50-3.40(6H, m); 3.99 (1H, m); 5.30(1H, s); 11.05 (1H, s). |
| 2,5,6,7-$(CH_3)_4$ | Colourless solid, mp 221° C. | Not recorded |
| 1,5,6,7-$(CH_3)_4$ | Colourless solid, mp 191° C. | Not recorded |
| 5-$CH_2CH_2CH_2$-6 | Brownish solid | 1.90-2.30(7H, m); 2.50-3.00(12H, m); 3.40(1H, m); 5.30(1H, s); 11.00(1H, s). |
| 7-$CH_3$-5-$CH_2CH_2CH_2$-6 | Cream solid, mp 214° C. | Not recorded |
| 5-Br-6,7-$(CH_3)_2$ | Light brown solid | 1.88-4.28(11H, m); 2.24 (3H, s); 2.39(3H, s); 5.31(1H, s); 11.20(1H, s). |

TABLE 7c

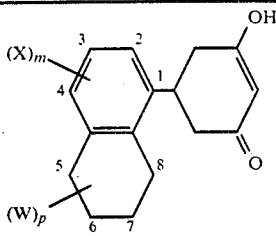

| $(X)_m + (W)_p$ | Appearance | Proton Chemical Shift δ in ppm (D$_6$-DMSO) |
|---|---|---|
| 2,3,4-(CH$_3$)$_3$ | Colourless solid. mp 214° C. | 1.60-1.80(4H, m); 2.10(6H, s); 2.20(3H, s); 2.30-3.30(8H, m); 3.80(1H, m); 5.30(1H, s); 11.00(1H, s). |
| 3,4-(CH$_3$)$_2$-2-OCH$_3$ | Brown solid | 1.70(4H, m); 2.10(3H, s); 2.20(3H, s); 2.40-3.30 (8H, m); 3.70(3H, s); 5.25 (1H, s); 11.00(1H, s). |

TABLE 7d

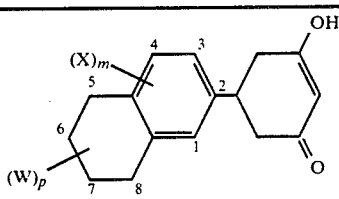

| $(X)_m + (W)_p$ | Appearance | Proton Chemical Shift δ in ppm (D$_6$-DMSO) |
|---|---|---|
| H | Pale yellow solid, mp 198° C. | Not recorded |

TABLE 7e

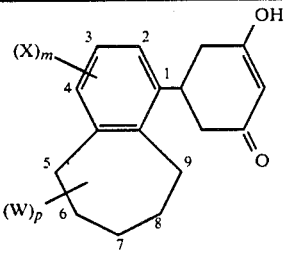

| $(X)_m + (W)_p$ | Appearance | Proton Chemical Shift δ in ppm (D$_6$-DMSO) |
|---|---|---|
| 2,3,4-(CH$_3$)$_3$ | Orange solid | 1.40(6H, m); 2.18(6H, s); 2.21(3H, s); 2.25-3.40(8H, m); 3.98(1H, m); 5.20(1H, s); 11.00(1H, s). |

EXAMPLE 29

The 2-acyl-5-arylcyclohexane-1,3-dione derivatives of formula XIII used in the preparation of the compounds of formula I were prepared from the corresponding 5-arylcyclohexane-1,3-dione derivatives of formula IX by acylation using the appropriate acyl derivative and following a procedure essentially the same as that described in Example 8 part (iii).

The majority of the 2-acyl-5-arylcyclohexane-1,3-dione derivatives of formula XIII were obtained as oils and were characterized by their nuclear magnetic resonance spectra. For convenience, proton nuclear magnetic resonance spectroscopic (pmr) data and/or melting point data is recorded in Table 8 below.

TABLE 8a

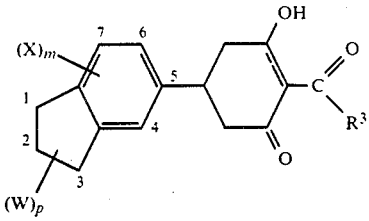

| $(X)_m + (W)_p$ | $R^3$ | Appearance | Proton Chemical Shift δ in ppm (CDCl$_3$) |
|---|---|---|---|
| H | C$_2$H$_5$ | Yellow solid, mp 98° C. | 1.10(3H, t); 2.00(2H, m); 2.50-3.40(11H, m); 7.00-7.40(3H, m); 18.00(1H, s). |
| H | n-C$_3$H$_7$ | Yellow solid, mp 92° C. | 1.17(3H, t); 1.65(2H, m); 2.06(2H, m); 2.68-3.21(11H, m); 6.95-7.14(3H, m); 18.00(1H, s). |
| 4,7-(CH$_3$)$_2$ | C$_2$H$_5$ | Yellow oil | 1.15(3H, t); 1.90-2.20(8H, m); 2.60-3.20(10H, m); 3.50 (1H, m); 6.80(1H, s); 18.20(1H, s). |
| 4,6-(CH$_3$)$_2$ | C$_2$H$_5$ | Yellow oil | 1.20(3H, t); 1.95-2.40(8H, m); 2.40-3.30(10H, m); 3.80(1H, m); 6.90(1H, s); 18.20(1H, s). |
| 4,6,7-(CH$_3$)$_3$ | C$_2$H$_5$ | Yellow oil | 1.10(3H, t); 1.80-2.30(11H, m); 2.40-3.60(10H, m); 3.90(1H, m); 18.10(1H, s). |
| 7-Br-4,6-(CH$_3$)$_2$ | C$_2$H$_5$ | Yellow oil | 1.15(3H, t); 2.00-2.80 (8H, m); 2.80-3.40 (10H, m); 3.80(1H, m); 18.10(1H, s). |
| 2,2,4,7-(CH$_3$)$_4$ | C$_2$H$_5$ | Orange oil | 1.00-1.25(9H, m); 2.14 (6H, s); 2.40-2.90(8H, m); 3.10(2H, q); 3.65 (1H, m); 6.78(1H, s); 18.20(1H, s). |
| 2,2,4,6,7-(CH$_3$)$_5$ | C$_2$H$_5$ | Yellow oil | 1.05-1.25(9H, m); 2.10 (3H, s); 2.20(6H, s); 2.20-3.40(10H, m); 3.80(1H, m); 18.10 (1H, s). |
| 2,2-(CH$_3$)$_2$ | C$_2$H$_5$ | Yellow oil | 1.00-1.25(9H, m); 2.60-3.40(11H, m); 6.80-7.20(3H, m); 18.20(1H, s). |
| 4,6-(CH$_3$)$_2$-7-SO$_2$N(CH$_3$)$_2$ | C$_2$H$_5$ | Yellow oil | 1.12(3H, t); 1.80-2.25(4H, m); 2.32(3H, s); 2.55-3.52(17H, m); 3.60-4.15(1H, m); 18.25(1H, s). |
| 4,7-(CH$_3$)$_2$-6-SO$_2$N(CH$_3$)$_2$ | C$_2$H$_5$ | Yellow oil | 1.12(3H, t); 1.90-2.25 (2H, m); 2.40(3H, s); 2.55(3H, s); 2.72(6H, s); 2.80-3.32(6H, m); 3.70(2H, q); 4.52-4.95 (1H, m); 18.20(1H, s). |
| 6-Br-4,7-(CH$_3$)$_2$ | C$_2$H$_5$ | Yellow oil | 1.20(3H, t); 1.95-3.25 (18H, m); 3.95(1H, m); 18.20(1H, s). |
| 4,7-(CH$_3$)$_2$-6-C$_2$H$_5$ | C$_2$H$_5$ | Yellow oil | 1.00-1.27(6H, m); 2.80 (2H, m); 2.20(3H, s); 2.30(3H, s); 2.40-3.30 (12H, m); 3.80(1H, m); 18.20(1H, s). |
| 7-Cl-4,6-(CH$_3$)$_2$ | C$_2$H$_5$ | Yellow oil | 1.15(3H, t); 1.80-2.35 (5H, m); 2.45(6H, s); 2.55-3.52(10H, m); 3.72-4.12(1H, m); 18.20(1H, s). |

TABLE 8a-continued

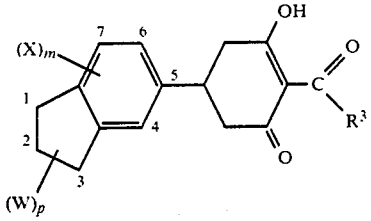

| $(X)_m + (W)_p$ | $R^3$ | Appearance | Proton Chemical Shift δ in ppm (CDCl$_3$) |
|---|---|---|---|
| 4-Cl-6,7-(CH$_3$)$_2$ | C$_2$H$_5$ | Yellow solid, mp 120° C. | Not recorded |
| 6-Br-4,7-(CH$_3$)$_2$ | n-C$_3$H$_7$ | Orange oil | 1.00(3H, t); 1.60(2H, m); 1.95-3.25(18H, m); 3.95(1H, m); 18.20 (1H, s). |
| 6-Cl-4,7-(CH$_3$)$_2$ | n-C$_3$H$_7$ | Orange oil | 1.00(3H, t); 1.70(2H, m); 1.95-3.20(18H, m); 3.95(1H, m); 18.10(1H, s). |
| 6-Cl-4,7-(CH$_3$)$_2$ | C$_6$H$_5$ | Yellow oil | 2.00(2H, m); 2.25(6H, s); 2.40-3.40(9H, m); 7.40(5H, m); 17.00(1H, s). |
| 2-CH$_3$ | C$_2$H$_5$ | Yellow oil | 1.00-1.15(6H, m); 2.30-3.40(12H, m); 6.80-7.40(3H, m); 18.20(1H, s). |
| 1,1,4,6,7-(CH$_3$)$_5$ | C$_2$H$_5$ | Orange oil | 1.10(3H, t); 1.38(6H, s); 1.90(2H, t); 2.20 (9H, s); 2.40-3.40(8H, m); 3.80(1H, m); 18.20 (1H, s). |
| 1,1,2,4,6,7-(CH$_3$)$_6$ | C$_2$H$_5$ | Yellow oil | 1.00-1.20(9H, m); 1.40 (3H, s); 2.00(1H, m); 2.25(9H, s); 2.25-3.40 (8H, m); 3.80(1H, m); 18.30(1H, s). |
| 1,1,2,4,6,7-(CH$_3$)$_6$ | n-C$_3$H$_7$ | Orange oil | 1.00-1.10(9H, m); 1.40(3H, s); 1.70(3H, m); 2.20(9H, s); 2.20-3.50(8H, m); 3.85(1H, m); 18.30(1H, s). |
| 3,4,6,7-(CH$_3$)$_4$ | n-C$_3$H$_7$ | Orange oil | 1.00-1.20(6H, m); 1.50-1.80(3H, m); 2.00-3.40(19H, m); 3.80(1H, m); 18.30(1H, s). |
| 2,4,6,7-(CH$_3$)$_4$ | n-C$_3$H$_7$ | Orange oil | 1.00(3H, t); 1.14(3H, d); 1.70(2H, m); 2.10 (3H, s); 2.20(3H, s); 2.20-3.40(11H, m); 3.85(1H, m); 18.30 (1H, s). |

TABLE 8b

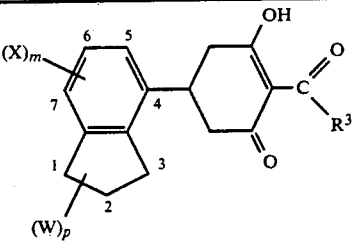

| $(X)_m + (W)_p$ | $R^3$ | Appearance | Proton Chemical Shift δ in ppm (CDCl$_3$) |
|---|---|---|---|
| 5,7-(CH$_3$)$_2$ | C$_2$H$_5$ | Orange oil | 1.20(3H, t); 1.90-2.40(8H, m); 2.50-3.20(10H, m); 3.60 (1H, m); 6.80(1H, s); 18.10(1H, s). |

TABLE 8b-continued

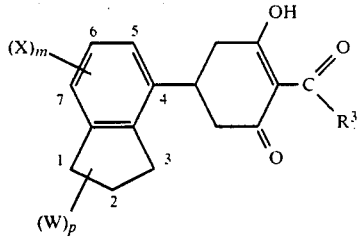

| $(X)_m + (W)_p$ | $R^3$ | Appearance | Proton Chemical Shift δ in ppm (CDCl$_3$) |
|---|---|---|---|
| 5,6,7-(CH$_3$)$_3$ | C$_2$H$_5$ | Orange oil | 1.20(3H, t); 1.95-2.20(11H, m); 2.60-3.30(10H, m); 3.70 (1H, m); 18.20(1H, s). |
| 6-Cl-5,7-(CH$_3$)$_2$ | C$_2$H$_5$ | Pale yellow solid, mp <50° C. | 1.20(3H, t); 1.85-2.35(5H, m); 2.45(3H, s); 2.52-3.35(10H, m); 3.52-4.10(1H, m); 18.22(1H, s). |
| 6-F-5,7-(CH$_3$)$_2$ | n-C$_3$H$_7$ | Yellow oil | 1.00(3H, t); 1.60(2H, m); 1.90-2.20(8H, m); 2.50-3.40(10H, m); 3.60(1H, m); 18.30(1H, s). |
| 5,6,7-(CH$_3$)$_3$ | C$_6$H$_5$ | Yellow oil | 2.00(2H, m); 2.20(6H, s); 2.30(3H, s); 2.30-3.40(8H, m); 3.85(1H, m); 7.50(5H, m); 17.00(1H, s). |
| 2,2,5,6,7-(CH$_3$)$_5$ | C$_2$H$_5$ | Orange oil | 1.00-1.20(9H, m); 2.10(6H, s); 2.20(3H, s); 2.40-3.20(10H, m); 3.70(1H, m); 18.20 (1H, s). |
| 2,2,5,6,7-(CH$_3$)$_5$ | n-C$_3$H$_7$ | Yellow oil. | 1.00(3H, t); 1.16(6H, s); 1.60(2H, m); 2.18 (3H, s); 2.20(3H, s); 2.25(3H, s); 2.40-3.20(10H, m); 3.70 (1H, m); 18.20(1H, s). |
| 2,2,5,6,7-(CH$_3$)$_5$ | C$_2$H$_5$ | Yellow oil | 1.00-1.40(6H, m); 1.87(2H, t); 2.20(6H, s); 2.30(3H, s); 2.60-3.40(8H, m); 3.95(1H, m); 18.20(1H, s). |
| 2,5,6,7-(CH$_3$)$_4$ | n-C$_3$H$_7$ | Orange oil | 1.00(3H, t); 1.15(3H, d); 1.70(2H, d); 2.20 (6H, s); 2.20-3.30 (11H, m); 2.23(3H, s); 3.79(1H, m); 18.30(1H, s). |
| 1,5,6,7-(CH$_3$)$_4$ | n-C$_3$H$_7$ | Orange oil | 1.10-1.20(6H, m); 1.60-1.90(4H, m); 2.18(3H, s); 2.20(3H, s); 2.21(3H, s); 2.30-3.40(9H, m); 3.75(1H, m); 18.30 (1H, s). |
| 5-CH$_2$CH$_2$CH$_2$-6 | C$_2$H$_5$ | Orange oil | 1.15(3H, t); 2.00-2.40(4H, m); 2.60-3.12(14H m); 3.63 (1H, m); 7.00(1H, s); 18.20(1H, s). |
| 5-CH$_2$CH$_2$CH$_2$-6 | n-C$_3$H$_7$ | Orange oil | 1.00(3H, t); 1.50(2H, m); 2.00-2.40(4H, m); 2.60-3.10(14H, m); 3.60(1H, m); 7.00(1H, s); 18.20(1H, s). |
| 7-CH$_3$-5-CH$_2$CH$_2$CH$_2$-6 | n-C$_3$H$_7$ | Yellow oil | 1.00(3H, t); 1.50(2H, m); 2.00-2.40(7H, m); 2.60-3.10(14H, m); 3.60(1H, m); 18.15(1H, s). |
| 5-Br-6,7-(CH$_3$)$_2$ | n-C$_3$H$_7$ | Brown oil | 1.00(3H, t); 1.50-3.60(13H, m); 2.24(3H, s); 2.39(3H, s); 3.80- |

TABLE 8b-continued

Structure: indane-substituted cyclohexenone with OH and C(=O)R³ group, positions labeled 1,2,3 on cyclopentane ring, 4,5,6,7 on benzene ring, with (X)ₘ and (W)ₚ substituents.

| (X)ₘ + (W)ₚ | R³ | Appearance | Proton Chemical Shift δ in ppm (CDCl₃) |
|---|---|---|---|
| | | | 4.20(1H, m); 18.30(1H, s). |
| 5,6,7-(CH₃)₃ | n-C₃H₇ | Orange oil | 1.00(3H, t); 1.70(2H, m); 2.05(2H, m); 2.21 (6H, s); 2.29(3H, s); 2.40–3.20(10H, m); 3.80(1H, m); 18.30 (1H, s). |

TABLE 8c

Structure: tetrahydronaphthalene-substituted cyclohexenone with OH and C(=O)R³ group.

| (X)ₘ + (W)ₚ | R³ | Appearance | Proton Chemical Shift δ in ppm (CDCl₃) |
|---|---|---|---|
| 2,3,4-(CH₃)₃ | C₂H₅ | Yellow oil | 1.18(3H, t); 1.80(4H, m); 2.20(6H, s); 2.30 (3H, s); 2.30–3.50 (10H, m); 3.92(1H, m); 18.20(1H, s). |
| 2,3,4-(CH₃)₃ | n-C₃H₇ | Yellow oil | 1.00(3H, t); 1.70(6H, m); 2.10(6H, s); 2.20 (3H, s); 2.20–3.40 (10H, m); 3.95(1H, m); 18.20(1H, s). |
| 3,4-(CH₃)₂-2-OCH₃ | n-C₃H₇ | Orange oil | 1.00(3H, t); 1.70(6H, m); 2.10(3H, s); 2.20 (3H, s); 2.40–3.30 (10H, m); 3.70(3H, s); 3.95(1H, m); 18.25 (1H, s). |

TABLE 8d

Structure: tetrahydronaphthalene (different connectivity) substituted cyclohexenone with OH and C(=O)R³ group.

| (X)ₘ + (W)ₚ | R³ | Appearance | Proton Chemical Shift δ in ppm (CDCl₃) |
|---|---|---|---|
| H | C₂H₅ | Yellow solid, mp 87° C. | 1.10(3H, t); 1.80(4H, m); 2.60–3.20(11H, m); 7.00–7.20(3H, m); 18.20(1H, s). |

TABLE 8e

Structure: benzocycloheptane-substituted cyclohexenone with OH and C(=O)R³ group.

| (X)ₘ + (W)ₚ | R³ | Appearance | Proton Chemical Shift δ in ppm (CDCl₃) |
|---|---|---|---|
| 2,3,4-(CH₃)₃ | n-C₃H₇ | Orange oil | 1.00(3H, t); 1.50–1.80 (8H, m); 2.20–2.30(9H, m); 2.30–3.40(10H, m); 3.95(1H, m); 18.20(1H, s). |

EXAMPLE 30

The majority of the compounds of the invention were obtained as oils and were characterized by, and can be identified by their nuclear magnetic resonance spectra. For convenience, proton nuclear magnetic resonance spectroscopic (pmr) data and/or melting point data is recorded in Table 9 below.

TABLE 9

| Compound No | Appearance | Proton Chemical Shift δ in ppm (CDCl₃) |
|---|---|---|
| 1 | Pale yellow oil | 1.09–1.39(6H, m); 1.90–2.13 (2H, m); 2.68–3.00(11H, m); 4.10 (2H, q); 7.04–7.23(3H, m); 14.90 (1H, s). |
| 3 | Yellow oil | 0.92–1.26(6H, m); 2.06(2H, m); 2.47–2.95(10H, m); 3.40(1H, m); 4.00(2H, q); 7.07–7.25(3H, m); 7.45–8.09(5H, m). |
| 4 | Yellow oil | 1.17(3H, t); 2.06(2H, t); 2.68–3.21(11H, m); 4.53(2H, d); 5.36 (2H, dofd); 5.91(1H, m); 6.95–7.14(3H, m); 14.95(1H, s). |
| 5 | Yellow oil | 0.98(3H, t); 1.32(3H, t); 1.58 (2H, m); 2.06(2H, m); 2.68–3.04 (11H, m); 4.10(2H, q); 6.93–7.14 (3H, m); 14.06(1H, s). |
| 6 | Yellow oil | 0.97(3H, t); 1.64(2H, m); 2.06 (2H, m); 2.75–2.95(10H, m); 3.15 (1H, m); 4.52(2H, d); 5.35 (2H, m); 5.89(1H, m); 6.98–7.14 (3H, m); 14.77(1H, s). |
| 7 | Yellow oil | 1.08–1.39(6H, m); 1.78(4H, m); 2.67–3.09(11H, m); 4.10 (2H, qJ=8Hz); 6.93–6.99(3H, m); 15.06(1H, s). |
| 8 | Yellow oil | 1.10–1.40(6H, m); 1.99–2.22 (8H, m); 2.76–3.02(10H, m); 3.56 (1H, m); 4.11(2H, q); 6.85 (1H, s); 15.02(1H, s). |
| 9 | Yellow oil | 1.11–1.41(6H, m); 1.96–2.38 (8H, m); 2.38–3.08(10H, m); 4.00–4.24(3H, m); 6.92(1H, s); 15.01(1H, s). |
| 10 | Yellow oil | 1.11–1.40(6H, m); 1.92–2.18 (5H, m); 2.33(3H, s); 2.40–3.14 (10H, m); 3.64(1H, m); 4.11(2H, q); 6.81(1H, s); 14.96(1H, s). |
| 11 | Pale yellow solid mp 99° C. | 1.12–1.95(6H, m); 2.03(5H, m); 2.30(6H, s); 2.63–3.07(10H, m); 4.01–4.21(3H, m); 14.97(1H, s). |
| 12 | Brown oil | 1.11–1.40(6H, m); 1.94–2.21 (8H, m); 2.29(3H, s); 2.76–3.00 (10H, m); 3.81(1H, m); 4.12(2H, q); 15.01(1H, s). |

TABLE 9-continued

| Compound No | Appearance | Proton Chemical Shift δ in ppm (CDCl₃) |
|---|---|---|
| 13 | Yellow oil | 1.12–1.41(6H, m); 1.96–2.27 (5H, m); 2.50(3H, s); 2.50–3.05 (10H, m); 3.94–4.24(3H, m); 14.96(1H, s). |
| 14 | Brown oil | 1.11–1.40(12H, m); 2.18(6H, s); 2.66–3.01(10H, m); 3.50(1H, m); 4.11(2H, q); 6.83(1H, s); 14.98 (1H, s). |
| 15 | Yellow oil | 1.12–1.40(12H, m); 2.14(3H, s); 2.19(3H, s); 2.29(3H, s); 2.43–2.98(10H, m); 3.95–4.24(3H, m); 14.95(1Hs). |
| 16 | Yellow oil | 1.14–1.39(12H, m); 2.70–3.00 (11H, m); 4.10(2H, q); 7.03–7.08 (3H, m); 15.02(1H, s). |
| 17 | Yellow oil | 1.12–1.42(6H, m); 2.08–2.23(4H, m); 2.37(3H, s); 2.62(3H, s); 2.75(6H, s); 2.86–3.50(8H, m); 4.10–4.25(3H, m); 15.20(1H, s). |
| 18 | Bone solid. mp 75–77° C. | 1.08–1.40(6H, m); 1.98–3.20(24H, m); 4.01–4.24(2H, q); 4.6–4.9 (1H, m); 15.00(1H, s). |
| 19 | Yellow oil | 1.11–1.40(6H, m); 2.40(2H, m); 2.31(6H, s); 2.32–2.98(10H, m); 3.95–4.24(3H, m); 14.96(1H, s). |
| 20 | Yellow oil | 1.04–1.41(9H, m); 2.07(2H, m); 2.23(3H, s); 2.33(3H, s); 2.33–2.99(12H, m); 3.85(1H, m); 4.12 (2H, q); 14.98(1H, s). |
| 21 | Orange oil | 1.13–1.41(6H, m); 1.97–3.30(18H, m); 3.90–4.10(1H, m); 4.01–4.25 (2H, q); 15.01(1H, s). |
| 22 | Solid. mp <50° C. | 1.12–1.41(6H, m); 1.95–2.50 (12H, m); 2.83–3.05(6H, m); 3.30–4.24(3H, m); 14.96(1H, s). |
| 23 | Yellow oil | 1.00(3H, t); 1.32(3H, t); 1.63 (2H, m); 2.06(2H, m); 2.33(6H, s); 2.33–2.91(10H, m); 4.11(3H, m); 15.03(1H, s). |
| 24 | Cream solid. mp 131° C. | 1.00(3H, t); 1.32(3H, t); 1.57 (2H, m); 1.90–2.20(2H, m); 2.27 (6H, s); 2.27–3.00(8H, m); 3.40–4.23(5H, m); 15.11(1H, s). |
| 25 | Brown oil | 1.32(3H, t); 2.00(2H, m); 2.30 (6H, s); 2.30–3.40(8H, m); 3.60–4.30(3H, m); 7.20(5H, m); 13.51 (1H, s). |
| 26 | Yellow oil | 1.11–1.41(6H, m); 1.96–2.20(2H, m); 2.30(3H, s); 2.44(3H, s); 2.59–3.40(10H, m); 3.60–3.8(1H, m); 4.01–4.25(2H, q); 15.09(1H, s). |
| 27 | Yellow oil | 1.12–1.41(6H, m); 1.75(4H, m); 2.17(3H, s); 2.20(3H, s); 2.35 (3H, s); 2.35–2.99(10H, m); 4.00–4.24(3H, m); 14.90(1H, s). |
| 28 | Yellow oil | 1.00(3H, t); 1.32(3H, t); 1.75 (6H, m); 2.18(3H, s); 2.21(3H, s); 2.35(3H, s); 2.35–3.40(10H, m); 3.90–4.23(3H, m); 15.07(1H, s). |
| 29 | Yellow oil | 1.00(3H, t); 1.32(3H, t); 1.69 (8H, m); 2.23(3H, s); 2.26(3H, s); 2.30(3H, s); 2.30–3.00(10H, m); 3.90–4.24(3H, m); 15.07(1H, s). |
| 30 | Yellow oil | 1.00(3H, t); 1.32(3H, t); 1.56 (6H, m); 2.13(3H, s); 2.21(3H, s); 2.21–3.02(10H, m); 3.95(4H, m); 4.10(2H, q); 15.04 (1H, s). |
| 31 | Pale orange solid, mp 270° C. (decomp.) | Not recorded |
| 32 | Yellow oil | 1.12–1.41(6H, m); 1.61(2H, m); 1.96–2.27(8H, m); 2.50(3H, s); 2.50–3.06(10H, m); 3.94–4.24 (3H, m); 7.45–7.64(3H, m); 7.98–8.09(2H, m). |
| 33 | White solid mp >250° C. | Not recorded |
| 34 | Yellow oil (decomp.) | 1.00(3H, t); 1.33(3H, t); 1.65 (2H, m); 1.97–2.25(8H, m); 2.25–3.03(10H, m); 3.60(1H, m); 4.11 (2H, q); 15.17(1H, s). |
| 35 | Cream solid. mp >260° C. | Not recorded |
| 36 | Cream solid. mp 240° C. | Not recorded |
| 37 | Yellow oil | 0.93(3H, t); 1.27(3H, t); 1.57 (2H, m); 2.11(2H, m); 2.15(3H, s); 2.20(6H, s); 2.30(3H, s); 2.37–3.17(10H, m); 3.51–4.26(3H, m). |
| 38 | Yellow oil | 0.87(3H, t); 1.19(3H, t); 1.40 (2H, m); 2.00(2H, m); 2.21(6H, s); 2.28(3H, s); 2.46(3H, s); 2.46–3.95(10H, m); 3.95–4.19(3H, m); 7.52(4H, m). |
| 39 | Yellow oil | 1.01(3H, t); 1.60(2H, m); 2.10 (2H, m); 2.21(6H, s); 2.29(3H, s); 2.29–3.40(10H, m); 3.70(1H, m); 4.64(2H, s); 5.81(2H, m); 13.90 (1H, s). |
| 40 | Green solid. mp 212° C. (decomp.) | Not recorded |
| 41 | Pale green solid. mp 231° C. (decomp.) | Not recorded |
| 42 | Yellow oil | 0.82–1.17(6H, m); 1.60(2H, m); 2.05(2H, m); 2.21(6H, s); 2.34 (3H, s); 2.38–3.47(10H, m); 3.94–4.01(3H, m); 8.26(4H, m). |
| 43 | Yellow oil | 0.83–1.06(15H, m); 1.18–1.60 (21H, m); 1.97(2H, m); 2.19(6H, s); 2.28(3H, s); 2.81–3.15(18H, m); 3.60–4.21(3H, m). |
| 44 | Yellow oil | 0.99(3H, t); 1.58(2H, m); 2.02 (2H, m); 2.21(6H, s); 2.29(3H, s); 2.29–3.10(10H, m); 3.74(1H, m); 4.11–4.20(1H, m); 4.36–4.51(2H, 4.89–4.98(1H, m); 14.13(1H, s). |
| 45 | Yellow oil | 1.32(3H, t); 2.00(2H, m); 2.22 (6H, s); 2.34(3H, s); 2.40–3.20 (8H, m); 3.90–4.30(3H, m); 7.40 (5H, m); 13.51(1H, s). |
| 46 | Yellow oil | 1.10–1.39(9H, m); 2.68–3.08(12H, m); 4.10(2H, q); 7.02–7.24(3H, m); 14.99(1H, s). |
| 47 | Yellow oil | 1.11–1.36(12H, m); 1.85(2H, m); 2.26(9H, s); 2.26–3.06(8H, m); 3.99–4.23(3H, m); 14.94(1H, s). |
| 48 | Yellow oil | 1.03–1.98(15H, m); 2.06–2.27 (10H, m); 2.27–3.06(8H, m); 3.79–4.24(3H, m); 14.94(1H, s). |
| 49 | Yellow oil | 0.92–1.59(15H, m); 1.75(2H, m); 2.06–2.27(10H, m); 2.27–3.01 (8H, m); 3.78–4.23(3H, m); 15.06 (1H, s). |
| 50 | Yellow oil | 0.92–1.78(6H, m); 1.32(3H, t); 1.50–1.80(3H, m); 2.17(3H, s); 2.31(3H, s); 2.34(3H, s); 2.17–3.40(10H, m); 3.70–4.24(3H, m); 15.08(1H, s). |
| 51 | Yellow oil | 1.00(3H, t); 1.16(3H, d); 1.32 (3H, t); 1.58(2H, m); 2.16(3H, s); 2.28(6H, s); 2.28–3.12(11H, m); 3.60–4.23(3H, m); 15.09(1H, s). |
| 52 | Pale yellow oil | 1.14–1.41(12H, m); 2.17(3H, s); 2.19(3H, s); 2.28(3H, s); 2.30–3.00(10H, m); 3.80(1H, m); 4.12 (2H, q); 15.01(1H, s). |
| 53 | Yellow oil | 1.00–1.40(12H, m); 1.60(2H, m); 2.16(3H, s); 2.19(3H, s); 2.28 (3H, s); 2.28–3.30(10H, m); 3.70 (1H, m); 4.11(2H, q); 15.13(1H, s). |
| 54 | Yellow oil | 1.11–1.41(12H, m); 1.84(2H, t); 2.16(3H, s); 2.19(3H, s); 2.33 (3H, s); 2.33–2.98(8H, m); 3.98–4.17(3H, m); 14.90(1H, s). |

TABLE 9-continued

| Compound No | Appearance | Proton Chemical Shift δ in ppm (CDCl$_3$) |
|---|---|---|
| 55 | Yellow oil | 0.92-1.40(10H, m); 1.60(2H, m); 2.20-3.17(19H, m); 3.50-3.85 (1H, m); 4.11(2H, q); 15.14(1H, s). |
| 56 | Pale yellow oil | 0.92-1.40(9H, m); 1.60(2H, m); 2.19(3H, s); 2.24(3H, s); 2.29 (3H, s); 2.19-3.29(11H, m); 3.90 (1H, m); 4.11(2H, q); 15.09(1H, s). |
| 57 | Yellow oil | 1.11-1.41(6H, m); 1.98-2.21 (4H, m); 2.77-3.00(14H, m); 3.58 (1H, m); 4.12(2H, q); 7.04(1H, s); 15.04(1H, s). |
| 58 | Yellow oil | 1.00(3H, t); 1.32(3H, t); 1.57 (2H, m); 2.06(4H, m); 2.77-3.00 (14H, m); 3.60(1H, m); 4.11(2H, q); 7.04(1H, s); 15.14(1H, s). |
| 59 | Yellow oil | 1.00(3H, t); 1.32(3H, t); 1.58 (2H, m); 2.07-2.28(7H, m); 2.73-3.03(14H, m); 3.40(1H, m); 4.11 (2H, q); 15.12(1H, s). |
| 60 | Yellow oil | 1.00(3H, t); 1.32(3H, t); 1.40-3.55(15H, m); 2.24(3H, s); 2.39 (3H, s); 4.11(2H, q); 15.16(1H, s) |
| 61 | Yellow oil | 1.01(3H, t); 1.32(3H, t); 1.61 (2H, m); 2.06(2H, m); 2.21(6H, s); 2.29(3H, s); 2.75-3.10(10H, m); 3.73(1H, m); 4.11(2H, q); 15.13 (1H, s). |

EXAMPLE 31

This non-limiting Example illustrates the preparation of formulations of the compounds of the invention.

a) Emulsifiable Concentrate

Compound No 61 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

b) Aqueous Suspension

Compound No 61 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

c) Emulsifiable Concentrate

Compound No 61 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

d) Dispersible Powder

Compound No 61 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

e) High Strength Concentrate

Compound No 61 (99 parts by weight), silica aerogel (0.5 parts by weight) and synthetic amorphous silica (0.5 parts by weight) were blended and ground in a hammer-mill to produce a powder having a particle size less than 200 microns.

f) Dusting Powder

Compound No 61 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part a), b) or c) above and then diluted with water, optionally containing a surface active agent and/or oil, to give aqueous compositions of the required concentration which were used, as described in Examples 32 and 33, in the evaluation of the pre-emergence and post-emergence herbicidal activity of the compounds.

EXAMPLE 32

The pre-emergent herbicidal activity of the compounds of the invention formulated as described in Example 31 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 10 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |

-continued

| | |
|---|---|
| Sf | Sunflower |

TABLE 10

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2.0 | 0 | 0 | 5 | 5 | 0 | 0 | 0 | 0 |
| 1 | 0.5 | 0 | 0 | 4 | 4 | 0 | 0 | 0 | 0 |
| 3 | 5.0 | 3 | 3 | 5 | 5 | 0 | 0 | 0 | 0 |
| 3 | 2.0 | 0 | 3 | 5 | 5 | 0 | 0 | 0 | 0 |
| 3 | 0.5 | 0 | 0 | 4 | 3 | 0 | 0 | 0 | 0 |
| 4 | 1.0 | 0 | 0 | 5 | 4 | 0 | 0 | 0 | 0 |
| 4 | 0.25 | 0 | 0 | 0 | 0 | 0 | 0 | 0 | 0 |
| 5 | 1.0 | 0 | 0 | 5 | 3 | 0 | 0 | 0 | 0 |
| 5 | 0.25 | 0 | 0 | 0 | 0 | 0 | 0 | 0 | 0 |
| 6 | 1.0 | 0 | 0 | 4 | 3 | 0 | 0 | 0 | 0 |
| 6 | 0.25 | 0 | 0 | 0 | 0 | 0 | 0 | 0 | 0 |
| 7 | 1.0 | 0 | 0 | 4 | 5 | 0 | 0 | 0 | 0 |
| 7 | 0.25 | 0 | 0 | 0 | 0 | 0 | 0 | 0 | 0 |
| 8 | 1.0 | 1 | 4 | 5 | 5 | 0 | 0 | 0 | 0 |
| 8 | 0.25 | 0 | 2 | 5 | 5 | 0 | 0 | 0 | 0 |
| 9 | 0.25 | 0 | 0 | 5 | 5 | 0 | 0 | 0 | 0 |
| 9 | 0.125 | 0 | 0 | 5 | 5 | 0 | 0 | 0 | 0 |
| 11 | 0.25 | 0 | 0 | 5 | 5 | 0 | 0 | 0 | 0 |
| 11 | 0.125 | 0 | 0 | 5 | 5 | 0 | 0 | 0 | 0 |
| 12 | 1.0 | 0 | 0 | 5 | 5 | 0 | 0 | 0 | 0 |
| 12 | 0.25 | 0 | 5 | 5 | 5 | 0 | 0 | 0 | 0 |
| 13 | 0.25 | 0 | 0 | 5 | 4 | 0 | 0 | 0 | 0 |
| 13 | 0.125 | 0 | 0 | 5 | 2 | 0 | 0 | 0 | 0 |
| 14 | 0.5 | 1 | 4 | 4 | 5 | 0 | 0 | 0 | 0 |
| 14 | 0.125 | 0 | 0 | 3 | 3 | 0 | 0 | 0 | 0 |
| 15 | 0.5 | 0 | 4 | 5 | 5 | 0 | 0 | 0 | 0 |
| 15 | 0.125 | 0 | 0 | 4 | 5 | 5 | 0 | 0 | 0 |
| 16 | 0.5 | 0 | 0 | 2 | 1 | 0 | 0 | 0 | 0 |
| 17 | 0.5 | 3 | 4/5 | 5 | 5 | 0 | 0 | 0 | 0 |
| 17 | 0.125 | 0 | 0 | 5 | 4 | 0 | 0 | 0 | 0 |
| 18 | 0.5 | 0 | 0 | 4 | 4/5 | 0 | 0 | 0 | 0 |
| 19 | 0.5 | 0 | 1 | 3 | 5 | 0 | 0 | 0 | 0 |
| 19 | 0.125 | 0 | 0 | 2 | 3 | 0 | 0 | 0 | 0 |
| 20 | 0.5 | 0 | 4 | 5 | 5 | 0 | 0 | 0 | 0 |
| 20 | 0.125 | 0 | 0 | 5 | 1 | 0 | 0 | 0 | 0 |
| 22 | 0.25 | 0 | 2 | 4 | 5 | 0 | 0 | 0 | 0 |
| 23 | 0.25 | 0 | 0 | 1 | 4 | 0 | 0 | 0 | 0 |
| 24 | 1.0 | 0 | 4 | 5 | 5 | 0 | 0 | 0 | 0 |
| 27 | 0.5 | 0 | 1 | 4 | 5 | 0 | 0 | 0 | 0 |
| 30 | 1.0 | 0 | 5 | 5 | 5 | 0 | 0 | 0 | 0 |
| 31 | 1.0 | 5 | 5 | 5 | 5 | 0 | 0 | 0 | 0 |
| 31 | 0.25 | 0 | 4/5 | 0 | 0 | 0 | 0 | 0 | 0 |
| 32 | 1.0 | 3 | 3 | 4 | 4 | 0 | 0 | 0 | 0 |
| 33 | 1.0 | 0 | 1 | 0 | 5· | 0 | 0 | 0 | 0 |
| 46 | 0.5 | 0 | 0 | 3 | 4 | 0 | 0 | 0 | 0 |
| 47 | 0.25 | 0 | 1 | 5 | 5 | 0 | 0 | 0 | 0 |
| 48 | 1.0 | 4 | 4 | 5 | 5 | 0 | 0 | 0 | 0 |
| 48 | 0.25 | 0 | 0 | 3 | 4 | 0 | 0 | 0 | 0 |
| 49 | 1.0 | 0 | 0 | 5 | 5 | 0 | 0 | 0 | 0 |
| 50 | 1.0 | 5 | 5 | 5 | 5 | 0 | 0 | 0 | 0 |
| 50 | 0.25 | 1 | 3 | 4/5 | 5 | 0 | 0 | 0 | 0 |
| 51 | 1.0 | 0 | 4 | 4 | 5 | 0 | 0 | 0 | 0 |
| 56 | 1.0 | 1 | 5 | 5 | 5 | 0 | 0 | 0 | 0 |
| 56 | 0.25 | 0 | 3 | 4 | 4 | 0 | 0 | 0 | 0 |
| 58 | 0.5 | 0 | 0 | 3 | 5 | 0 | 0 | 0 | 0 |
| 60 | 1.0 | 0 | 4/5 | 5 | 5 | 0 | 0 | 0 | 0 |

EXAMPLE 33

The post-emergent herbicidal activity of the compounds of the invention formulated as described in Example 31 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 11 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese Millet |
| P | Peas |
| Ip | Ipomea |
| Ms | Mustard |
| Sf | Sunflower |

TABLE 11

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2.0 | 3 | 5 | 5 | 5 | 0 | 0 | 0 | 0 |
| 1 | 0.5 | 0 | 5 | 5 | 5 | 0 | 0 | 0 | 0 |
| 3 | 5.0 | 0 | 5 | 5 | 5 | 0 | 0 | 0 | 0 |
| 3 | 2.0 | 0 | 5 | 5 | 5 | 0 | 0 | 0 | 0 |
| 3 | 0.5 | 0 | 3 | 4 | 5 | 0 | 0 | 0 | 0 |
| 4 | 1.0 | 1 | 5 | 5 | 5 | 0 | 0 | 0 | 0 |
| 4 | 0.25 | 0 | 4 | 5 | 5 | 0 | 0 | 0 | 0 |
| 5 | 1.0 | 3 | 5 | 5 | 5 | 0 | 0 | 0 | 0 |
| 5 | 0.25 | 0 | 5 | 5 | 5 | 0 | 0 | 0 | 0 |
| 6 | 1.0 | 3 | 5 | 5 | 5 | 0 | 0 | 0 | 0 |
| 6 | 0.25 | 0 | 5 | 5 | 5 | 0 | 0 | 0 | 0 |
| 7 | 1.0 | 0 | 5 | 5 | 5 | 0 | 0 | 0 | 0 |
| 7 | 0.25 | 0 | 4 | 5 | 5 | 0 | 0 | 0 | 0 |
| 8 | 1.0 | 5 | 5 | 5 | 5 | 0 | 0 | 0 | 0 |
| 8 | 0.25 | 1 | 5 | 5 | 5 | 0 | 0 | 0 | 0 |
| 9 | 0.25 | 3 | 5 | 5 | 5 | 0 | 0 | 0 | 0 |
| 9 | 0.125 | 2 | 5 | 5 | 5 | 0 | 0 | 0 | 0 |
| 10 | 0.25 | 2 | 5 | 5 | 5 | 0 | 0 | 0 | 0 |
| 10 | 0.125 | 0 | 5 | 5 | 5 | 0 | 0 | 0 | 0 |
| 11 | 0.25 | 4 | 5 | 5 | 5 | 0 | 0 | 0 | 0 |
| 11 | 0.125 | 3 | 5 | 5 | 5 | 0 | 0 | 0 | 0 |
| 12 | 1.0 | 3 | 5 | 5 | 5 | 0 | 0 | 0 | 0 |
| 12 | 0.25 | 0 | 3 | 5 | 5 | 0 | 0 | 0 | 0 |
| 13 | 0.25 | 3 | 5 | 5 | 5 | 0 | 0 | 0 | 0 |
| 13 | 0.125 | 0 | 5 | 5 | 5 | 0 | 0 | 0 | 0 |
| 14 | 0.5 | 5 | 5 | 5 | 5 | 0 | 0 | 0 | 0 |
| 14 | 0.125 | 4 | 4 | 3 | 5 | 0 | 0 | 0 | 0 |
| 15 | 0.5 | 5 | 5 | 5 | 5 | 0 | 0 | 0 | 0 |
| 15 | 0.125 | 4 | 5 | 5 | 5 | 0 | 0 | 0 | 0 |
| 16 | 0.5 | 0 | 3 | 5 | 5 | 0 | 0 | 0 | 0 |
| 16 | 0.125 | 0 | 0 | 5 | 5 | 0 | 0 | 0 | 0 |
| 17 | 0.5 | 4/5 | 5 | 5 | 5 | 0 | 0 | 0 | 0 |
| 17 | 0.125 | 3 | 5 | 5 | 5 | 0 | 0 | 0 | 0 |
| 18 | 0.5 | 0 | 0 | 4 | 5 | 0 | 0 | 0 | 0 |
| 18 | 0.125 | 0 | 0 | 2 | 5 | 0 | 0 | 0 | 0 |
| 19 | 0.5 | 4 | 5 | 5 | 5 | 0 | 0 | 0 | 0 |
| 19 | 0.125 | 2 | 4 | 5 | 5 | 0 | 0 | 0 | 0 |
| 20 | 0.5 | 4 | 5 | 5 | 5 | 0 | 0 | 0 | 0 |
| 20 | 0.125 | 3 | 4 | 5 | 5 | 0 | 0 | 0 | 0 |
| 21 | 0.125 | 0 | 0 | 2 | 4 | 0 | 0 | 0 | 0 |
| 22 | 0.25 | 0 | ¾ | 5 | 5 | 0 | 0 | 0 | 0 |
| 22 | 0.0625 | 0 | ¾ | 4/5 | 5 | 0 | 0 | 0 | 0 |
| 23 | 0.25 | 0 | ¾ | 4/5 | 5 | 0 | 0 | 0 | 0 |
| 24 | 1.0 | 0 | 5 | 5 | 5 | 0 | 0 | 0 | 0 |
| 24 | 0.25 | 0 | 4 | 2 | 3 | 0 | 0 | 0 | 0 |

TABLE 11-continued
POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 26 | 0.125 | 0 | 1 | 0 | 5 | 0 | 0 | 0 | 0 |
| 27 | 0.5 | 3 | 4/5 | 5 | 5 | 0 | 0 | 0 | 0 |
| 27 | 0.125 | 0 | 3 | 4 | 5 | 0 | 0 | 0 | 0 |
| 28 | 0.25 | 0 | 0 | 4 | 4 | 0 | 0 | 0 | 0 |
| 29 | 0.25 | 0 | 0 | 3 | 1 | 0 | 0 | 0 | 0 |
| 30 | 1.0 | ¾ | 5 | 5 | 5 | 0 | 0 | 0 | 0 |
| 30 | 0.25 | 0 | 2 | 0 | 0 | 0 | 0 | 0 | 0 |
| 31 | 1.0 | 3 | 5 | 5 | 5 | 0 | 0 | 0 | 0 |
| 31 | 0.25 | 0 | 5 | 5 | 5 | 0 | 0 | 0 | 0 |
| 31 | 0.0625 | 0 | 5 | 4 | 5 | 0 | 0 | 0 | 0 |
| 32 | 1.0 | 3 | 5 | 5 | 5 | 0 | 0 | 0 | 0 |
| 32 | 0.25 | 0 | 5 | 0 | 0 | 0 | 0 | 0 | 0 |
| 33 | 1.0 | 0 | 5 | 5 | 5 | 0 | 0 | 0 | 0 |
| 33 | 0.25 | 0 | 5 | 4/5 | 5 | 0 | 0 | 0 | 0 |
| 37 | 1.0 | 3 | 5 | 5 | 5 | 0 | 0 | 0 | 0 |
| 37 | 0.25 | 0 | 5 | 4 | 5 | 0 | 0 | 0 | 0 |
| 46 | 0.5 | 4 | 1 | 5 | 5 | 0 | 0 | 0 | 0 |
| 46 | 0.125 | 3 | 2 | 5 | 5 | 0 | 0 | 0 | 0 |
| 47 | 0.25 | 0 | 0 | 3 | 4 | 0 | 0 | 0 | 0 |
| 48 | 1.0 | 1 | 4/5 | 5 | 5 | 0 | 0 | 0 | 0 |
| 48 | 0.25 | 0 | 1 | 0 | 2 | 0 | 0 | 0 | 0 |
| 49 | 1.0 | 1 | 4/5 | 4 | 5 | 0 | 0 | 0 | 0 |
| 49 | 0.25 | 0 | 1 | 0 | 2 | 0 | 0 | 0 | 0 |
| 50 | 1.0 | 5 | 5 | 5 | 5 | 0 | 0 | 0 | 0 |
| 50 | 0.25 | 3 | 5 | 5 | 5 | 0 | 0 | 0 | 0 |
| 51 | 1.0 | 5 | 5 | 5 | 5 | 0 | 0 | 0 | 0 |
| 51 | 0.25 | 4 | 5 | 5 | 5 | 0 | 0 | 0 | 0 |
| 51 | 0.0625 | 2 | 5 | 5 | 5 | 0 | 0 | 0 | 0 |
| 52 | 0.125 | 0 | 0 | 0 | 2 | 0 | 0 | 0 | 0 |
| 53 | 0.25 | 0 | 0 | 0 | 0 | 0 | 0 | 0 | 0 |
| 54 | 0.25 | 0 | 0 | 3 | 4 | 0 | 0 | 0 | 0 |
| 55 | 1.0 | 0 | ¾ | 3 | 3 | 0 | 0 | 0 | 0 |
| 55 | 0.25 | 0 | 2 | 1 | 2 | 0 | 0 | 0 | 0 |
| 56 | 1.0 | 1 | 5 | 5 | 5 | 0 | 0 | 0 | 0 |
| 56 | 0.25 | 0 | 5 | 3 | 4 | 0 | 0 | 0 | 0 |
| 57 | 0.5 | 0 | 0 | 4/5 | 5 | 0 | 0 | 0 | 0 |
| 58 | 0.5 | 0 | 2 | 4 | 5 | 0 | 0 | 0 | 0 |
| 59 | 0.25 | 0 | 4 | 3 | 5 | 0 | 0 | 0 | 0 |
| 60 | 1.0 | 1 | 5 | 5 | 5 | 0 | 0 | 0 | 0 |
| 60 | 0.25 | 0 | 5 | 5 | 5 | 0 | 0 | 0 | 0 |
| 61 | 0.125 | 0 | 4 | 4 | 5 | 0 | 0 | 0 | 0 |
| 61 | 0.031 | 0 | 4 | 3 | 4 | 0 | 0 | 0 | 0 |

EXAMPLE 34

This Example illustrates the selective herbicidal activity of compounds of the invention.

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Tables 12 and 13 below. Damage to test plants was assessed after 26 days on a scale of 0 to 9 where 0 is 0 to 10% damage and 9 is complete kill. The degree of herbicidal damage was assessed by comparison with untreated control plants and the results are given in Tables 12 and 13 below. A dash (—) means that no experiment was carried out.

TABLE 12

| | | POST-EMERGENCE HERBICIDAL ACTIVITY | | | | | | | | | | |
|---|---|---|---|---|---|---|---|---|---|---|---|---|
| Compound No | APPLICATION Rate (kg/ha) | TEST PLANT | | | | | | | | | | |
| | | Mz | Rc | Sy | Ct | Sg | Ec | Dg | St | Sh | Pm | Sf | Ei |
| 53 | 0.02 | 1 | 2 | — | — | 1 | 9 | 8 | 7 | 1 | 4 | 7 | 8 |
| 61 | 0.025 | 4 | 0 | — | — | 6 | 9 | 9 | 5 | 2 | 3 | 7 | 9 |

The names of the test plants were as follows:

| Mz | Maize |
|---|---|
| Rc | Rice |
| Sy | Soyabean |
| Ct | Cotton |
| Sg | Sorghum |
| Ec | Echinochloa crus-gali |
| Dg | Digitaria sanguinalis |
| St | Setaria viridis |
| Sh | Sorghum halepense |
| Pm | Panicum maximum |
| Sf | Setaria faberii |
| Ei | Eleusine indica |

TABLE 13

| | | POST-EMERGENCE HERBICIDAL ACTIVITY | | | | | | | |
|---|---|---|---|---|---|---|---|---|---|
| Compound No | APPLICATION Rate (kg/ha) | TEST PLANT | | | | | | | |
| | | Ww | Br | Av | Al | Bs | Ll | St | Ap |
| 1 | 0.12 | 0 | — | 8 | 7 | — | — | 7 | — |
| 9 | 0.06 | 2 | — | 8 | 9 | 4 | 8 | 8 | 8 |
| 10 | 0.08 | 0 | 2 | 9 | 9 | 0 | 9 | 8 | 9 |
| 10 | 0.06 | 0 | — | 9 | 8 | 0 | 9 | 7 | 9 |
| 11 | 0.06 | 2 | — | 8 | 9 | 1 | 8 | 9 | 9 |

The names of the test plants were as follows:

| Ww | Winter wheat |
|---|---|
| Br | Spring barley |
| Av | Avena fatua |
| Al | Alopecurus myosuroides |
| Bs | Bromus sterilis |
| Ll | Lolium parenne |
| Ap | Apera spica venti |
| St | Setaria viridis |

We claim:
1. A compound of formula XIII

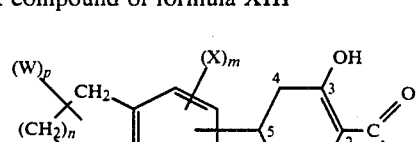

wherein
W, which may be the same or different, are selected from the group consisting of $C_1$ to $C_6$ alkyl, $C_2$ to $C_6$ alkenyl and $C_2$ to $C_6$ alkynyl;
X, which may be the same or different, are selected from the group consisting of: halogen; nitro; cyano; $C_1$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)-carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)-sulfamoyl; N,N-di($C_1$ to $C_6$ alkyl)sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^8R^9$ wherein $R^8$ and $R^9$ are independently selected from the group consisting of hydrogen; $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof; and the group $-(CH_2)_g-$ which bridges two adjacent carbon atoms of the benzene ring and wherein q is an integer selected from 2 to 5;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

p is zero or an integer selected from 1 to 4;

n is zero or an integer selected from 1 to 3;

m is zero or an integer selected from 1 to 3.

2. A compound according to claim 1, said compound being 2-propanoly-3-hydroxy-5-(5,6,7-trimethylindan-4-yl)cyclohex-2-en-1-one.

* * * * *